United States Patent
Lee et al.

(10) Patent No.: US 10,873,031 B2
(45) Date of Patent: Dec. 22, 2020

(54) P-DOPED CONJUGATED SMALL MOLECULAR ELECTROLYTE AND ORGANIC ELECTRONIC DEVICES USING THE SAME

(71) Applicant: GWANGJU INSTITUTE OF SCIENCE AND TECHNOLOGY, Gwangju (KR)

(72) Inventors: Kwanghee Lee, Gwangju (KR); Seoung-Ho Lee, Gwangju (KR); Jong-Hoon Lee, Gwangju (KR); Song-Yi Jeong, Gwangju (KR)

(73) Assignee: GWANGJU INSTITUTE OE SCIENCE AND TECHNOLOGY, Gwangju (KR)

( * ) Notice: Subject to any disclaimer, the term of this patent is extended or adjusted under 35 U.S.C. 154(b) by 583 days.

(21) Appl. No.: 14/757,459

(22) Filed: Dec. 23, 2015

(65) Prior Publication Data

US 2016/0181541 A1  Jun. 23, 2016

(30) Foreign Application Priority Data

Dec. 23, 2014 (KR) .......................... 10-2014-0187563

(51) Int. Cl.
*H01L 51/00* (2006.01)
*C07C 309/24* (2006.01)
(Continued)

(52) U.S. Cl.
CPC ........ *H01L 51/0052* (2013.01); *C07C 309/24* (2013.01); *H01L 51/0039* (2013.01);
(Continued)

(58) Field of Classification Search
CPC ............. H01L 51/4273; H01L 51/0036; H01L 51/0039; H01L 51/0043; H01L 51/0052; H01L 51/442; H01L 51/5056; C07C 2603/18; C07C 309/24; C07C 2103/18; Y02E 10/549
See application file for complete search history.

(56) References Cited

U.S. PATENT DOCUMENTS

| | | | | |
|---|---|---|---|---|
| 5,586,001 A | * | 12/1996 | Amano | H01G 9/025 252/62.2 |
| 2006/0160265 A1 | * | 7/2006 | Morii | H01L 51/0003 438/87 |
| 2013/0068305 A1 | * | 3/2013 | Lee | C08G 61/02 136/263 |

OTHER PUBLICATIONS

Shi, Wei; Wang, Lei; Huang, Fei; Liu, Ransheng; Yang, Wei; Cao, Yong, Anionic triphenylamine- and fluorene-based conjugated polyelectrolyte as a hole-transporting material for polymer light-emitting diodes, Polymer International (2009), 58(4), 373-379 (Year: 2009).*

* cited by examiner

Primary Examiner — Jennifer A Chriss
Assistant Examiner — Sean M DeGuire
(74) Attorney, Agent, or Firm — Hauptman Ham, LLP

(57) ABSTRACT

Disclosed are a p-doped conjugated small molecular electrolyte containing a compound represented by Formula 1 and an organic electronic device using the same as a hole transport material.

$$[Ar_2—Ar_1—Ar_2]^+ \qquad \text{<Formula 1>}$$

wherein, in Formula 1, $Ar_1$ is any one selected from the following Compound Group 1, $Ar_2$ is any one selected from the following Compound Group 2a or the following Compound Group 2b, and superscript "+" in the square bracket indicates an oxidized portion of a main chain of the small molecule.

1 Claim, 12 Drawing Sheets

(51) Int. Cl.
*H01L 51/42* (2006.01)
*H01L 51/50* (2006.01)
*H01L 51/44* (2006.01)

(52) U.S. Cl.
CPC ...... *H01L 51/4273* (2013.01); *C07C 2603/18* (2017.05); *H01L 51/0036* (2013.01); *H01L 51/0043* (2013.01); *H01L 51/442* (2013.01); *H01L 51/5056* (2013.01); *Y02E 10/549* (2013.01)

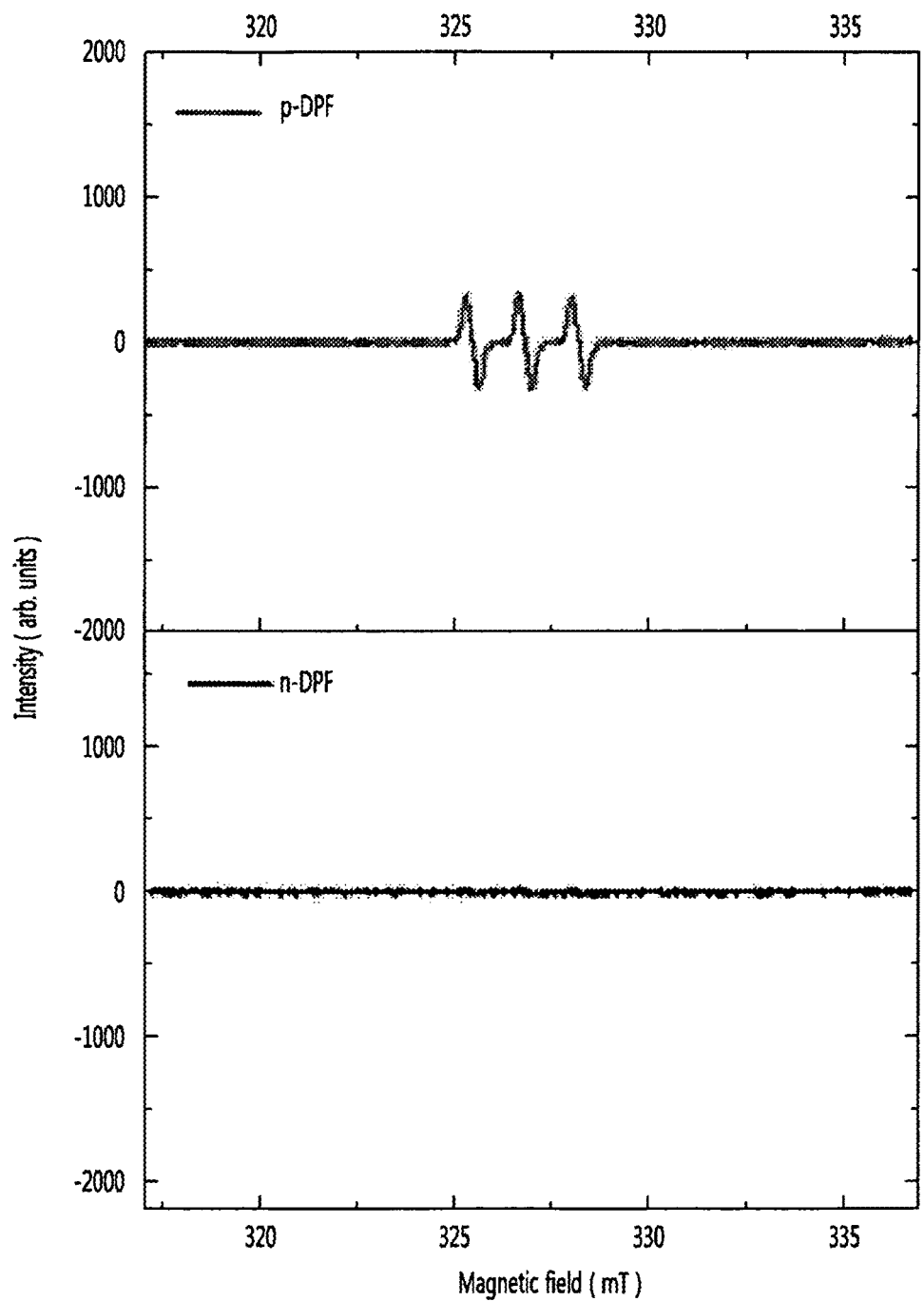

P-DOPED CONJUGATED SMALL MOLECULAR ELECTROLYTE AND ORGANIC ELECTRONIC DEVICES USING THE SAME

CROSS-REFERENCE TO RELATED APPLICATIONS

This application claims the benefit of Korean Patent Application No. 10-2014-0187563, filed on Dec. 23, 2014, entitled "P-DOPED CONJUGATED SMALL MOLECULAR ELECTROLYTE AND ORGANIC ELECTRONIC DEVICES USING THE SAME", which is hereby incorporated by reference in its entirety into this application.

BACKGROUND

1. Technical Field

The present disclosure relates to a p-doped conjugated small molecular electrolyte and an organic electronic device using the same.

2. Description of the Related Art

Since an organic light emitting device (OLED) and an organic solar cell (OSC) have advantages, such as simple structure of thin film, lightweight, convenient carrying, low cost process in manufacturing, and flexibleness, they are being actively studied recently. However, the energy level between the metal electrode and organic materials needs to be controlled due to the structural characteristics of these organic electronic devices. For this reason, various "interfacial layers" have been introduced between the metal electrode and organic materials. Such interfacial layers form an ohmic contact between the metal electrode and organic materials by controlling the work function of the electrode effectively. Conventional interfacial materials ever developed are inappropriate for organic electronic devices requiring printing techniques since their characteristics are expressed only via complicated deposition process. In the case of PEDOT:PSS, a typical hole transport material, which is solution-processable, however, severe quenching of excitons occurs at the interface with the active layer, and since PEDOT:PSS exhibits a strong acidity, it may oxidize the anode to have a bad influence on life-cycle and efficiency of devices. Further, in the case of conjugated polyelectrolytes (CPEs) and non-conjugated polyelectrolytes (non-CPEs) that have been used for the efficient electron injection between metal cathode and organic materials, and p-doped conjugated polyelectrolytes (p-CPEs) that have been used for the efficient hole injection between anode and organic materials, they all are print-processable, however, reproducibility of the material synthesis is low since they consist of polymer, and they have the batch-to-batch problem that the solubility for solvent varies. These problems are obstructive factors to make polyelectrolytes commercialized although the polyelectrolytes can control the work function effectively. Therefore, the present disclosure is to overcome said problems and to provide with a hole transport layer material based on an electrolyte consisting of not polymer but small molecules (low molecular weight compounds), and such hole transport layer material has not been reported yet.

SUMMARY

It is one aspect of the present disclosure to provide a conjugated small molecular electrolyte (CSE) which is solution-processable due to its water solubility and neutrality and usable as a hole transport material since there is no concern about the anode oxidation, and has a perfect reproducibility in synthesis or research on device characteristics.

It is another aspect of the present disclosure to provide an organic electronic device having enhanced life-cycle, high efficiency and reproducibility by using the p-doped conjugated small molecular electrolyte as a hole transport material.

It should be noted that objects of the present disclosure are not limited to the above-mentioned object; and other objects of the present disclosure will be apparent to those skilled in the art from the following descriptions.

In accordance with one aspect of the present disclosure, a p-doped conjugated small molecular electrolyte containing a compound represented by Formula 1 is provided.

$[Ar_2—Ar_1—Ar_2]^+$  <Formula 1>

In Formula 1, $Ar_1$ is any one selected from the following Compound Group 1, $Ar_2$ is any one selected from the following Compound Group 2a or the following Compound Group 2b, and superscript "+" in the square bracket indicates an oxidized portion of a main chain of the small molecule.

<Compound Group 1>

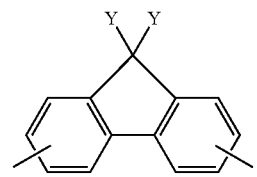

(01)

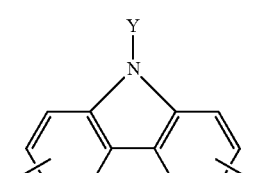

(02)

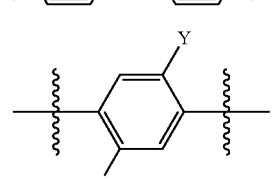

(03)

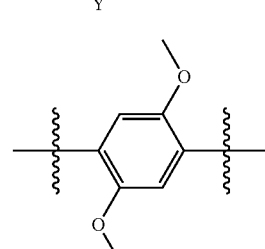

(04)

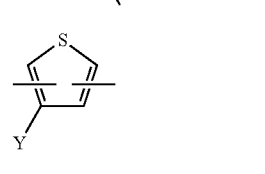

(05)

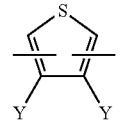

(06)

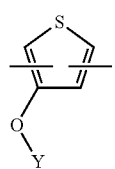 (07)
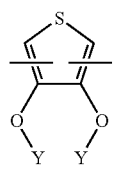 (08)
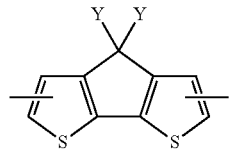 (09)
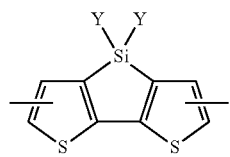 (10)
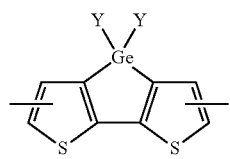 (11)
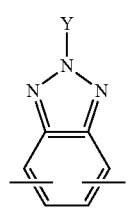 (12)
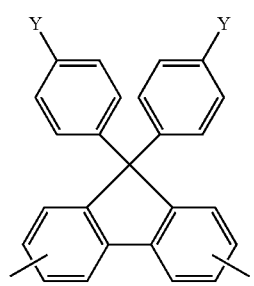 (13)
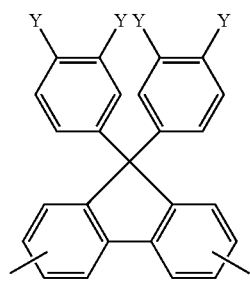 (14)
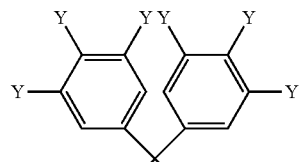 (15)
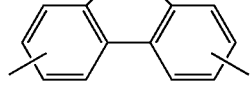 (16)
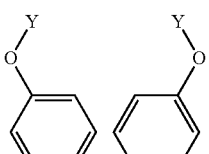 (17)
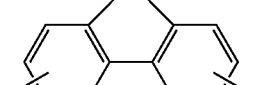 
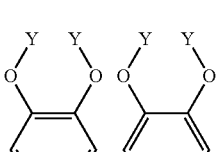 (18)
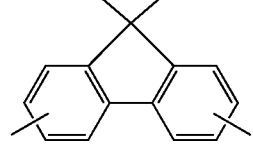 
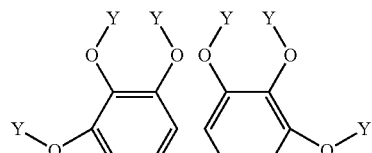 
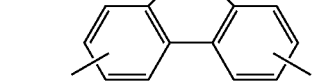 (19)
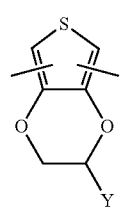

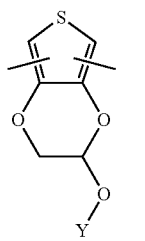
(20)

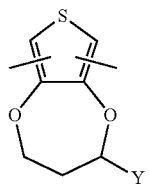
(21)

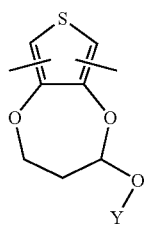
(22)

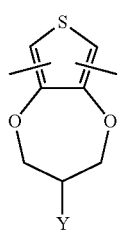
(23)

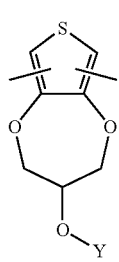
(24)

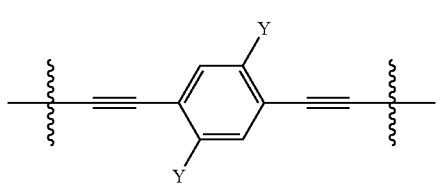
(25)

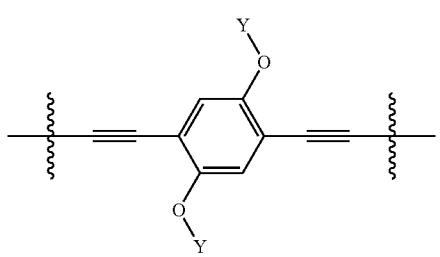
(26)

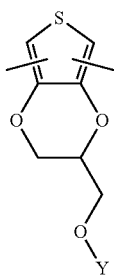
(27)

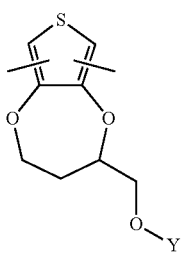
(28)

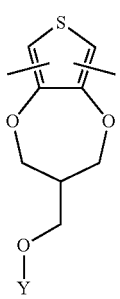
(29)

(wherein, in each compound selected from the Compound Group 1, independently, at least one of Ys is —$C_nH_{2n}$—$P^-$ (n is an integer between 1 and 20, $P^-$ is any one selected from the group consisting of $SO_3^-$, $PO_3^{2-}$ and $CO_2^-$), and the rest of Ys is —$C_nH_{2n}$—$P^-Q^+$ (n is an integer between 1 and 20, $P^-$ is any one selected from the group consisting of $SO_3^-$, $PO_3^{2-}$, and $CO_2^-$, $Q^+$ is any one selected from the group consisting of $H^+$, $Li^+$, $Na^+$, $K^+$, $Rb^+$, $Cs^+$, $N^+H_4$, and $N^+R_1R_2R_3R_4$, and $R_1$, $R_2$, $R_3$ and $R_4$ are each independently any one selected from C1 to C11 alkyl groups).)

<Compound Group 2a>

(01)

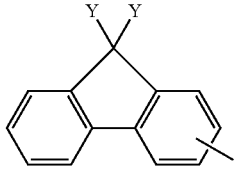
(02)

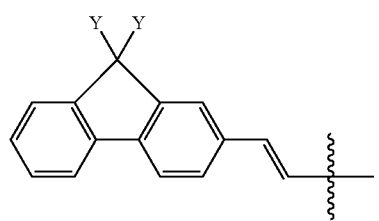
(03)
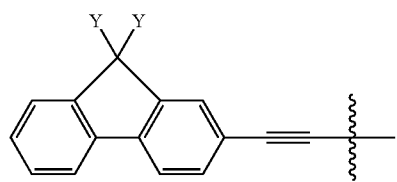
(04)
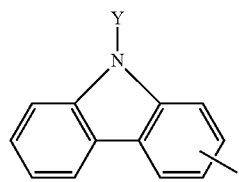
(05)
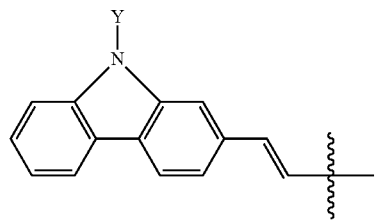
(06)
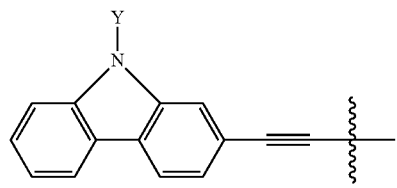
(07)
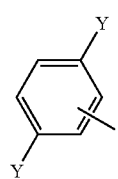
(08)
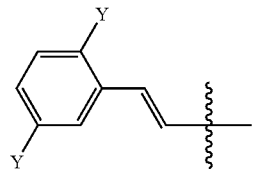
(09)
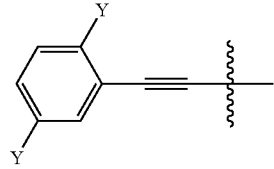
(10)
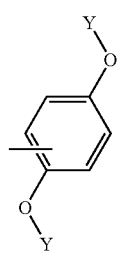
(11)
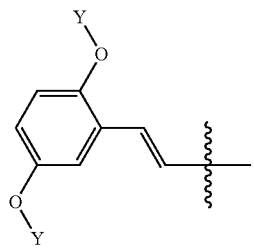
(12)
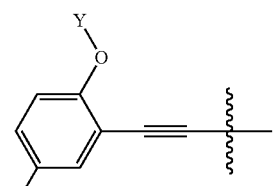
(13)
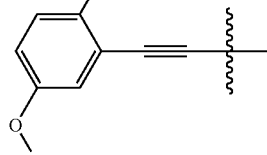
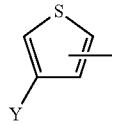
(14)
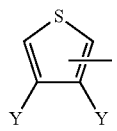
(15)
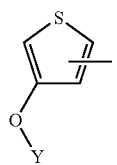
(16)
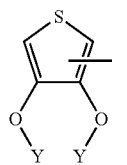
(17)
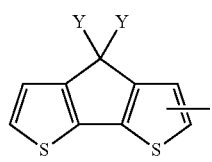
(18)

(19) 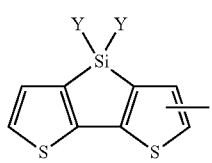
(20) 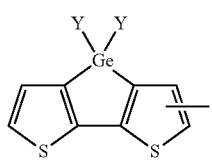
(21) 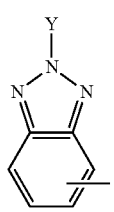
(22) 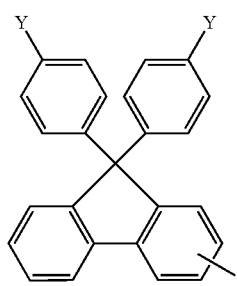
(23) 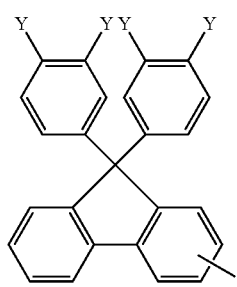
(24) 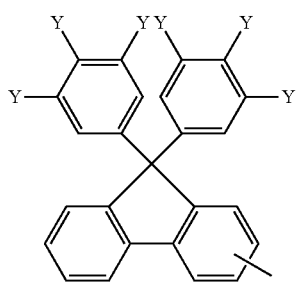
(25) 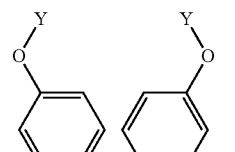
(26) 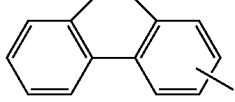
(27) 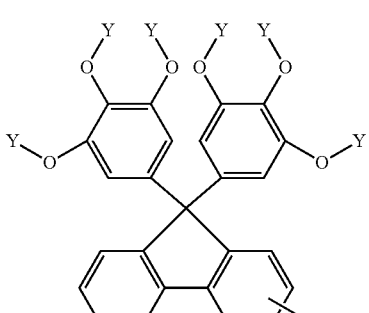
(28) 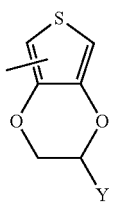
(29) 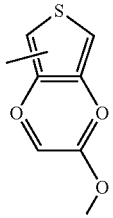
(30) 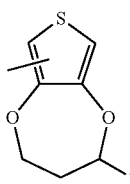

-continued

(31) 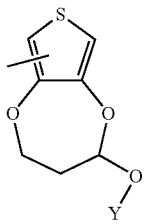

(32) 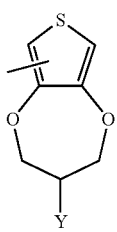

(33) 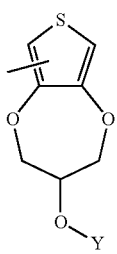

(34) 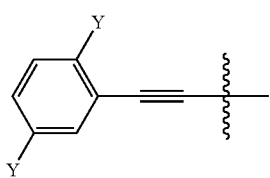

(35) 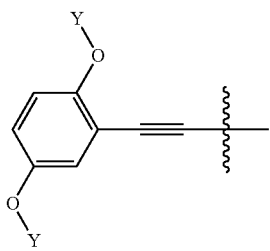

(36) 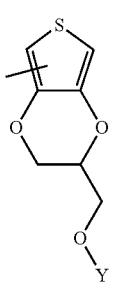

-continued

(37) 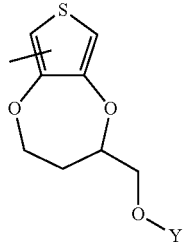

(38) 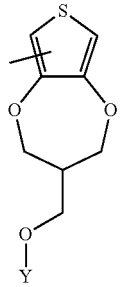

(wherein, in each compound selected from the Compound Group 2a, independently;

all Ys are —$C_nH_{2n}$—$P^-Q^+$ (n is an integer between 1 and 20, $P^-$ is any one selected from the group consisting of $SO_3^-$, $PO_3^{2-}$ and $CO_2^-$, $Q^+$ is any one selected from the group consisting of $H^+$, $Li^+$, $Na^+$, $K^+$, $Rb^+$, $Cs^+$, $N^+H_4$, and $N^+R_1R_2R_3R_4$, $R_1$, $R_2$, $R_3$ and $R_4$ are each independently any one selected from C1 to C11 alkyl groups), or at least one of Ys is —$C_nH_{2n}$—$P^-$ (n is an integer between 1 and 20, $P^-$ is any one selected from the group consisting of $SO_3^-$, $PO_3^{2-}$ and $CO_2^-$), and the rest of Ys is —$C_nH_{2n}$—$P^-Q^+$ (n is an integer between 1 and 20, $P^-$ is any one selected from the group consisting of $SO_3^-$, $PO_3^{2-}$, and $CO_2^-$, $Q^+$ is any one selected from the group consisting of $H^+$, $Li^+$, $Na^+$, $K^+$, $Rb^+$, $Cs^+$, $N^+H_4$, and $N^+R_1R_2R_3R_4$, and $R_1$, $R_2$, $R_3$ and $R_4$ are each independently any one selected from C1 to C11 alkyl groups).)

<Compound Group 2b>

(01) 

(02) 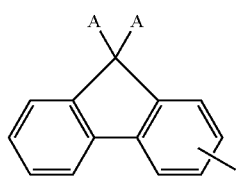

(03) 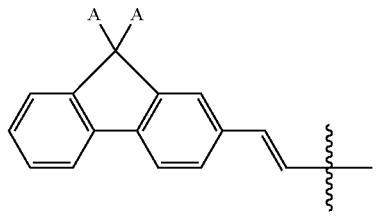

-continued
(04) 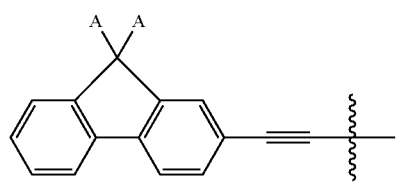
(05) 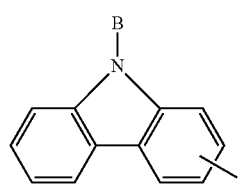
(06) 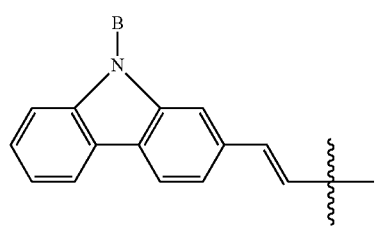
(07) 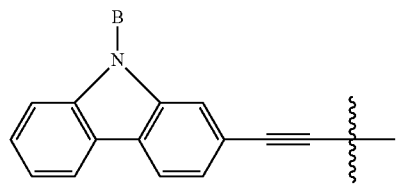
(08) 
(09) 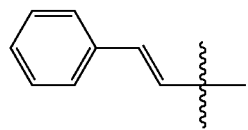
(10) 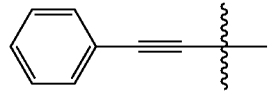
(11) 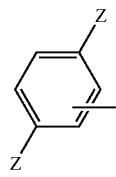
(12) 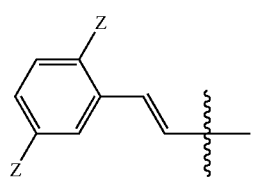
-continued
(13) 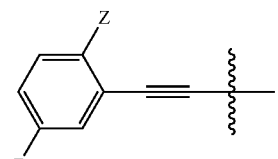
(14) 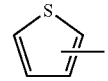
(15) 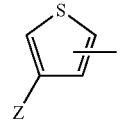
(16) 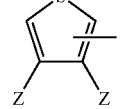
(17) 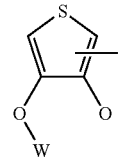
(18) 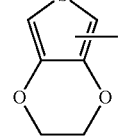
(19) 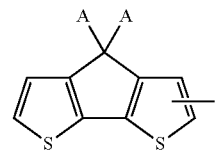
(20) 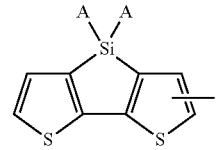
(21) 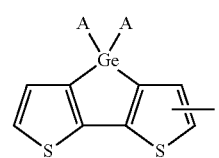
(22) 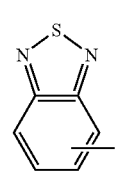

-continued

(23) 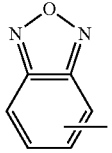

(24) 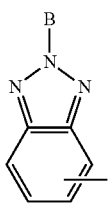

(25) 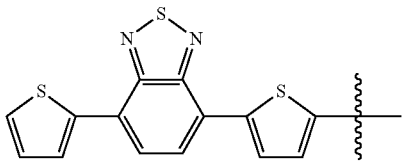

(26) 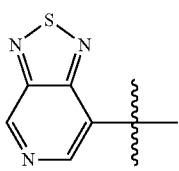

(27) 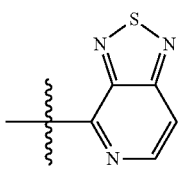

(28) 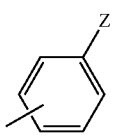

(29) 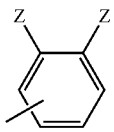

(30) 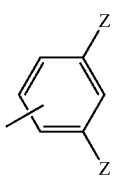

(31) 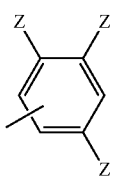

-continued

(32) 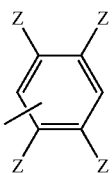

(33) 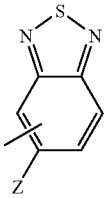

(34) 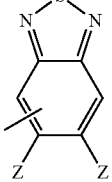

(35) 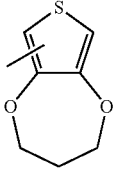

(36) 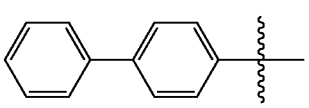

(wherein, in the Compound Group 2b, A is each independently any one selected from the group consisting of —H, —NR$_2$, —NH$_2$, —OH, —OR, —NHC(=O)R, —OC(=O)R, —R, —CH=CR$_2$, F, Cl, Br, and I, B is each independently any one selected from the group consisting of —H, —R, —CH=CR$_2$, F, Cl, Br, and I, Z is each independently any one selected from the group consisting of —NR$_2$, —NH$_2$, —OH, —OR, —NHC(=O)R, —OC(=O)R, —R, —CH=CR$_2$, F, Cl, Br, I, —C(=O)R, —C(=O)OR, and —C(=O)NR$_1$R$_2$, W is each independently any one selected from —H and —R, and R, R$_2$, R$_3$ and R$_4$ are each independently any one selected from C1 to C20 alkyl groups.)

In accordance with another aspect of the present disclosure, an organic electronic device comprising a first electrode; a small molecular electrolyte layer comprising the p-doped conjugated small molecular electrolyte on the first electrode; an organic active layer on the small molecular electrolyte layer; and a second electrode on the organic active layer is provided.

According to the present disclosure, the batch-to-batch problem that the solubility for solvent varies can be reduced, the doped state can be controlled by adjusting the electron density with various oxidizing agents and functional groups introduced into the p-type conjugated small molecule, and, as a result, the change in the work function can be finely controlled so that a high efficiency solar cell or an OLED having high-performance luminous characteristics can be prepared.

BRIEF DESCRIPTION OF THE DRAWINGS

The above and other aspects, features and advantages of the present disclosure will become apparent from the following description of exemplary embodiments given in conjunction with the accompanying drawings, in which:

FIG. 12 shows electron spin resonance (ESR) spectra of p-doped conjugated small molecular electrolyte (p-DPF) and non-oxidized DPF (n-DPF) according to an embodiment of the present disclosure.

DETAILED DESCRIPTION

Figure 1:
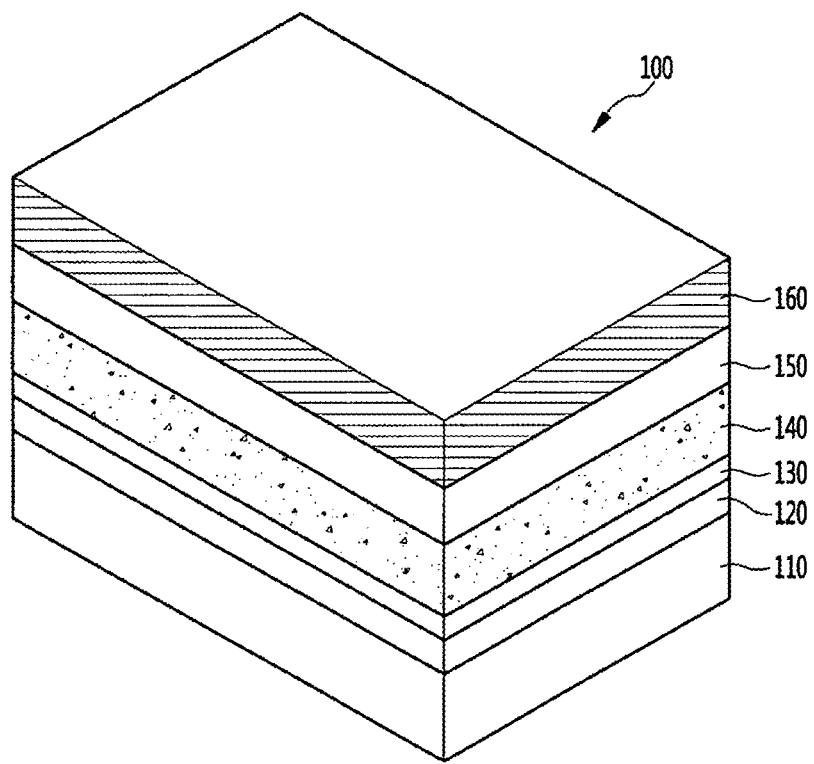
FIG. 1 is a schematic view illustrating an organic electronic device according to an embodiment of the present disclosure.

Hereinafter, exemplary embodiments of the present disclosure will be described in detail with reference to the accompanying drawings so as to enable those skilled in the art to easily practice the exemplary embodiments. However, exemplary embodiments of the present disclosure may be modified in various different ways and are not limited to those illustrated herein. In the accompanying drawings, non-essential elements are omitted in order not to unnecessarily obscure the gist of the present disclosure. Further, like reference numerals are used to denote like elements throughout the specification.

As used herein, a phrase "an element A on an element B" refers to that the element A may be disposed directly on the element B and/or the element A may be disposed indirectly on the element B via another element C.

Throughout the detailed descriptions, the terms "comprising" and "including" should not be interpreted as being restricted to the means listed thereafter; it does not exclude other elements or steps, unless explicitly stated otherwise. As used herein, the expression "step of" does not mean "step for."

As used herein, the term "conjugated polyelectrolytes (CPEs)" may refer to a compound with a molecular weight of 10,000 to 1,000,000, and the term "conjugated small molecular electrolytes (CSEs)" may refer to a small (low) molecular weight compound used for the synthesis of the CPEs with a molecular weight of 10 to 10,000. The molecular weight is not absolute value but may be somewhat changed.

The present disclosure relates to a p-doped conjugated small molecular electrolyte and an organic electronic device using the same.

The present inventors have found that a new hole transport material having no concern about the corrosion of electrode can be simply fabricated from small molecules, which is used in the synthesis of conventional conjugated polymer that has been difficult to be used as a hole transport layer, and have reached the present disclosure.

Particularly, n-type conjugated polyelectrolytes (n-CPEs) represented by exemplary Formula 3, which have been used as an electron transport layer (ETL) before, reduce the work function of metals, and, for this reason, they have been used as a cathode interfacial layer only.

<Formula 3>

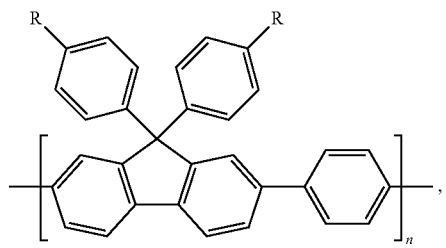

-continued

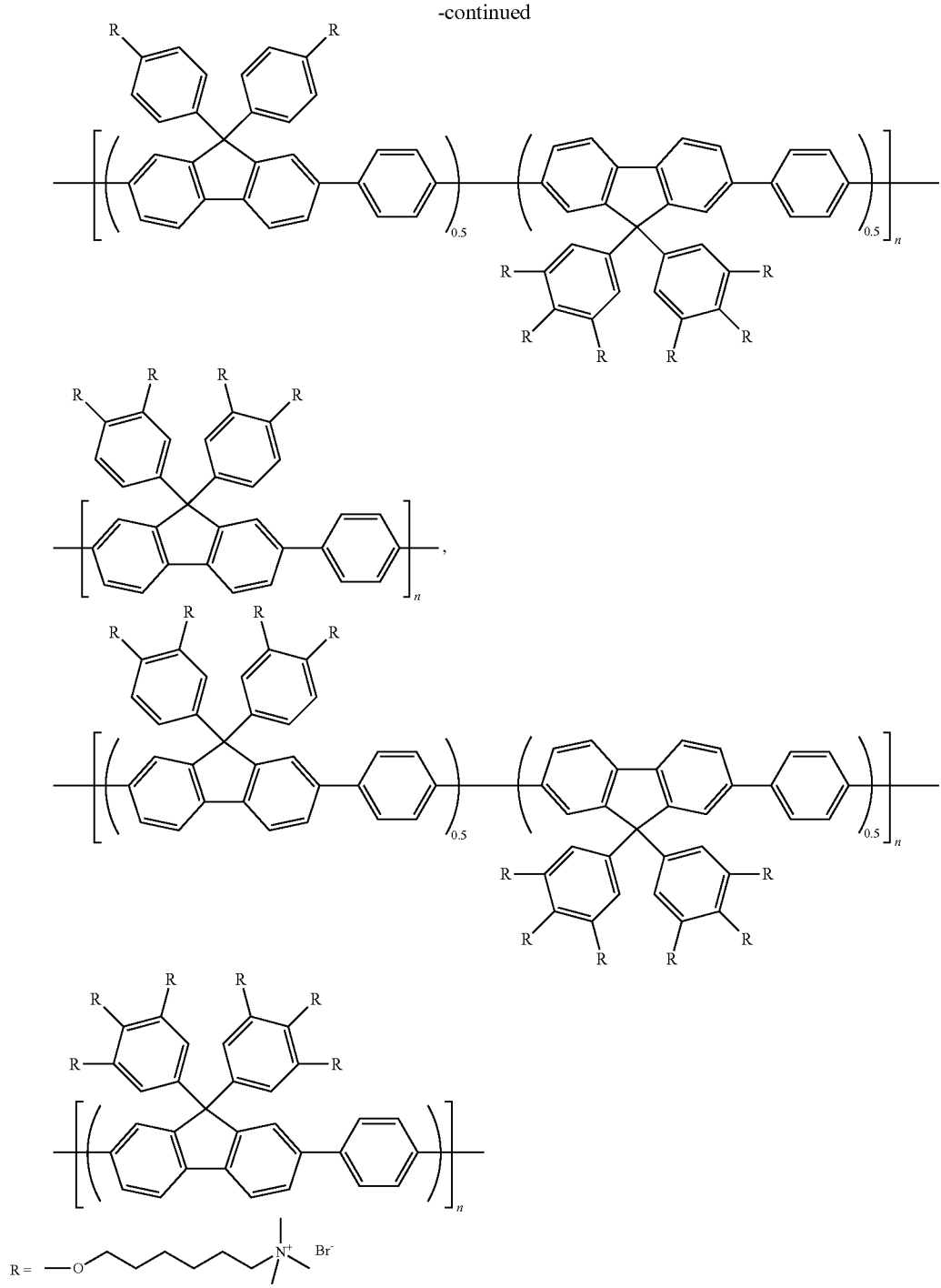

However, it was confirmed that small molecules used in the synthesis of these n-type conjugated polyelectrolytes is treated with oxidizing agent to form p-type conjugated small molecular electrolytes which can act as a hole transport layer (HTL). The p-type conjugated small molecular electrolyte thus formed generate a dipole pointing toward the opposite direction to that of n-types, and can "increase" or "decrease" the work function of metal electrode in electronic devices by 1 eV or more, where such change in the work function can be finely adjusted by the doped state, hence the ohmic contact of the anode in organic electronic devices with organic materials becomes efficient. The p-type conjugated small molecular electrolytes having small molecular structure can reduce the corrosion of a metal anode due to its neutrality and has no batch-to-batch problem that can be caused in polymer synthesis, hence it can exhibit a perfect reproducibility in synthesis or research on device characteristics.

The p-doped conjugated small molecular electrolyte of the present disclosure comprises a compound represented by Formula 1.

$$[Ar_2-Ar_1-Ar_2]^+ \qquad <\text{Formula 1}>$$

In Formula 1, $Ar_1$ is any one selected from the following Compound Group 1,
$Ar_2$ is any one selected from the following Compound Group 2a or the following Compound Group 2b, and
superscript "+" in the square bracket indicates an oxidized portion of a main chain of the small molecule.
<Compound Group 1>
(01)
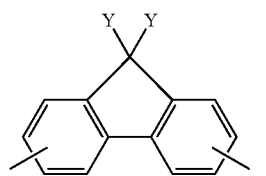
(02)
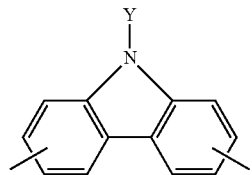
(03)
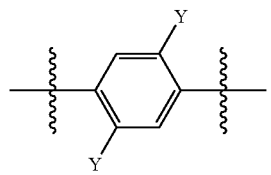
(04)
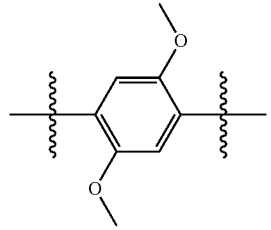
(05)
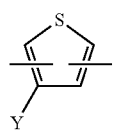
(06)
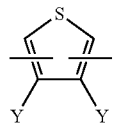
(07)
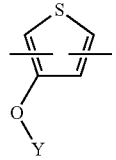
(08)
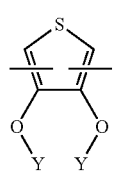
(09)
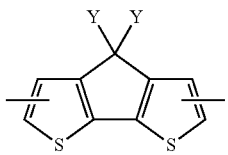
(10)
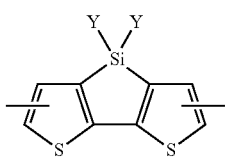
(11)
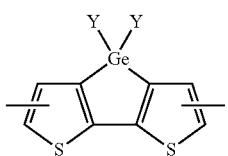
(12)
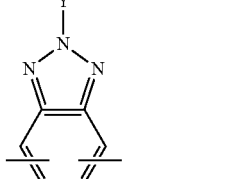
(13)
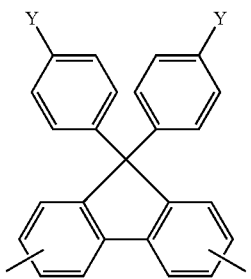
(14)
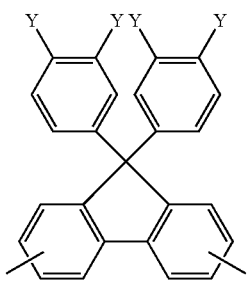
(15)
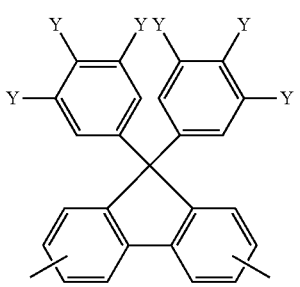

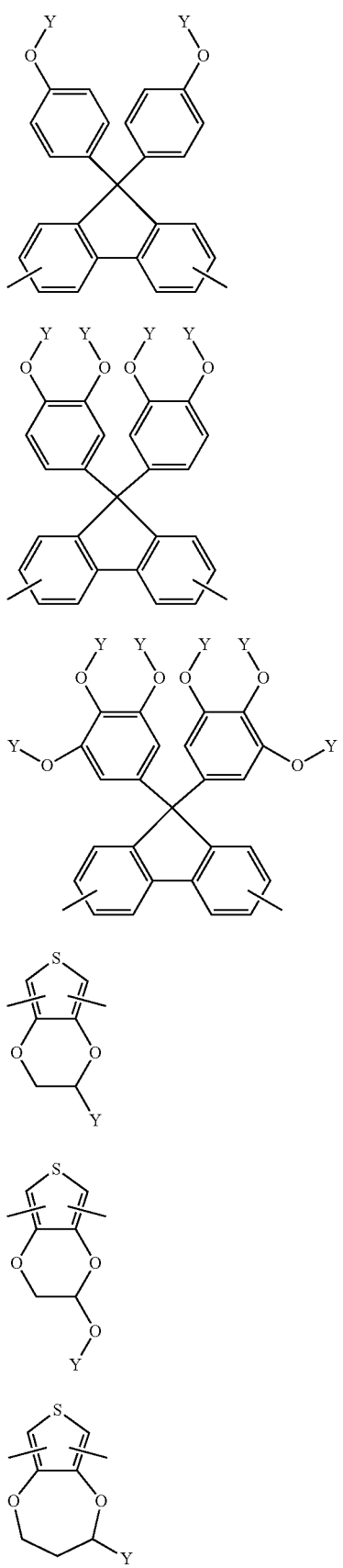
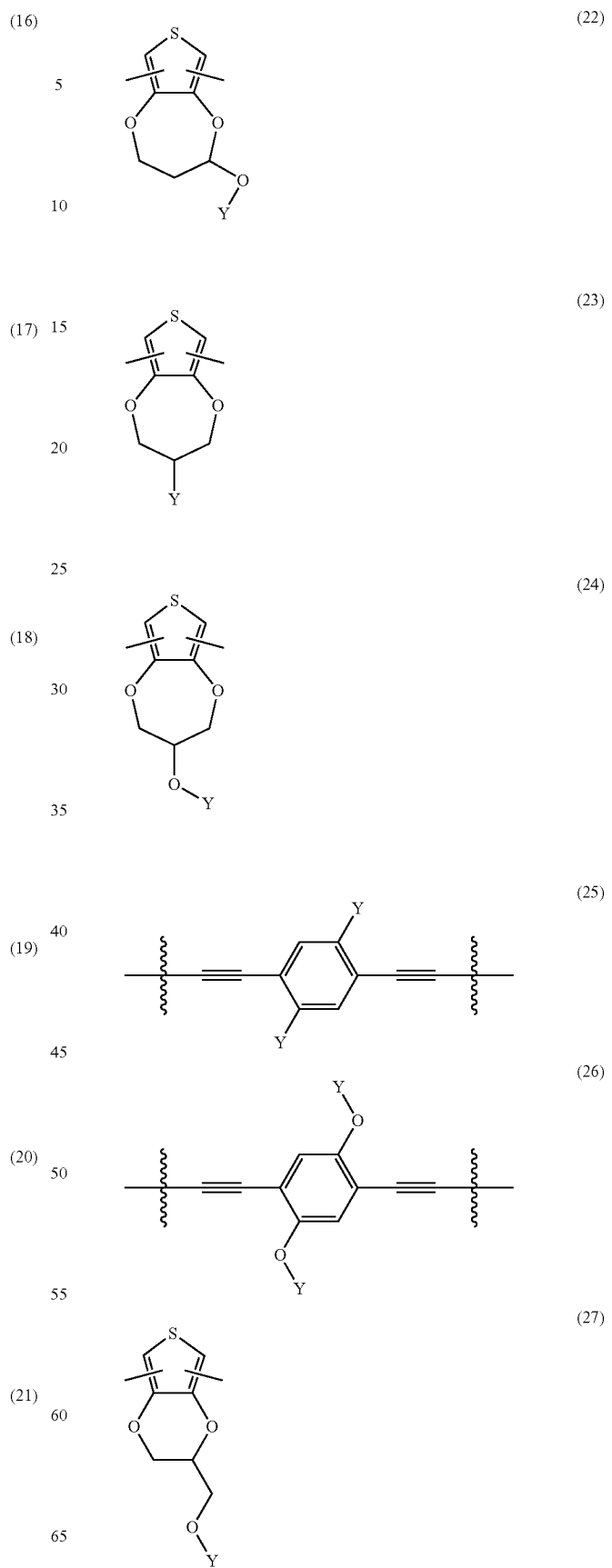

-continued

(28)
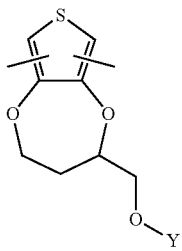

(29)
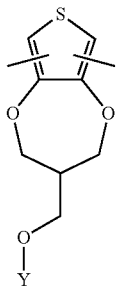

In each compound selected from the Compound Group 1, independently, at least one of Ys is —$C_nH_{2n}$—$P^-$ (n is an integer between 1 and 20, $P^-$ is any one selected from the group consisting of $SO_3^-$, $PO_3^{2-}$ and $CO_2^-$), and the rest of Ys is —$C_nH_{2n}$—$P^-Q^+$ (n is an integer between 1 and 20, $P^-$ is any one selected from the group consisting of $SO_3^-$, $PO_3^{2-}$, and $CO_2^-$, $Q^+$ is any one selected from the group consisting of $H^+$, $Li^+$. $Na^+$, $K^+$, $Rb^+$, $Cs^+$, $N^+H_4$, and $N^+R_1R_2R_3R_4$, and $R_1$, $R_2$, $R_3$ and $R_4$ are each independently any one selected from C1 to C11 alkyl groups).

<Compound Group 2a>

(01)
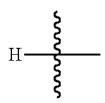

(02)
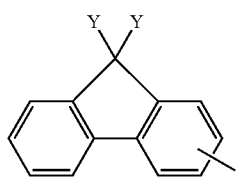

(03)
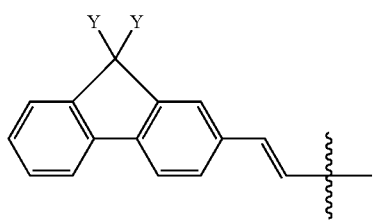

(04)
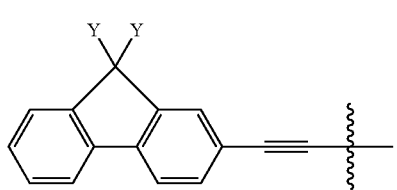

-continued

(05)
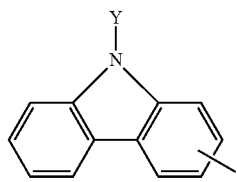

(06)
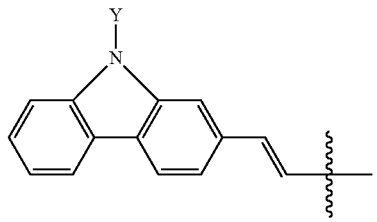

(07)
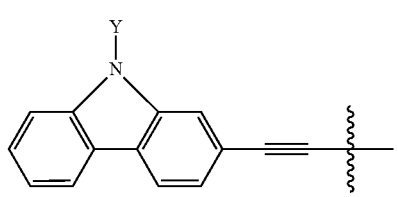

(08)
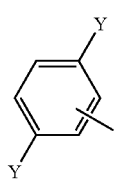

(09)
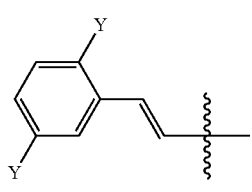

(10)
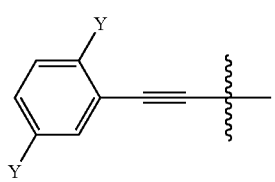

(11)
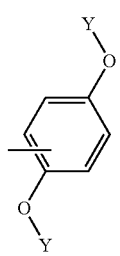

-continued
(12)
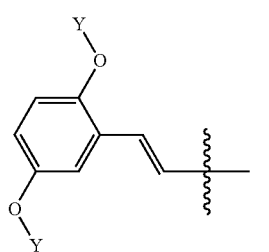
(13)
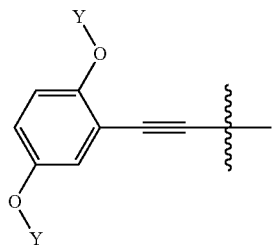
(14)
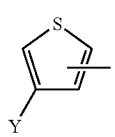
(15)
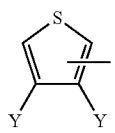
(16)
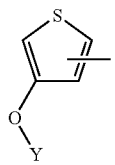
(17)
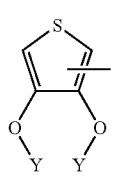
(18)
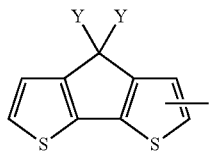
(19)
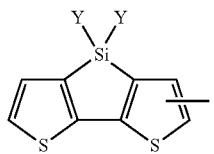
(20)
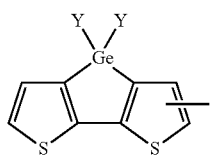
-continued
(21)
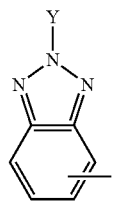
(22)
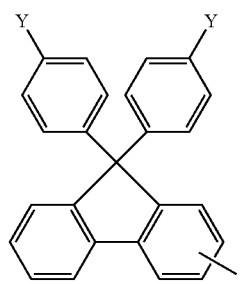
(23)
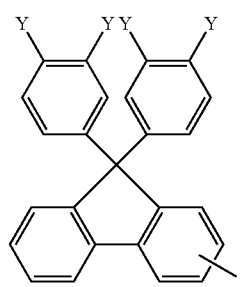
(24)
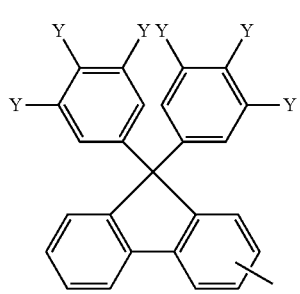
(25)
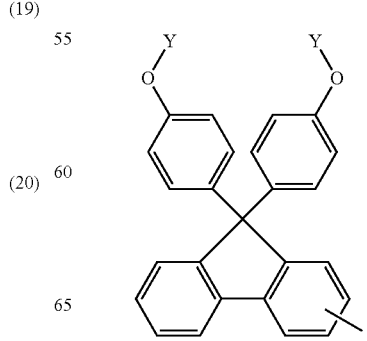

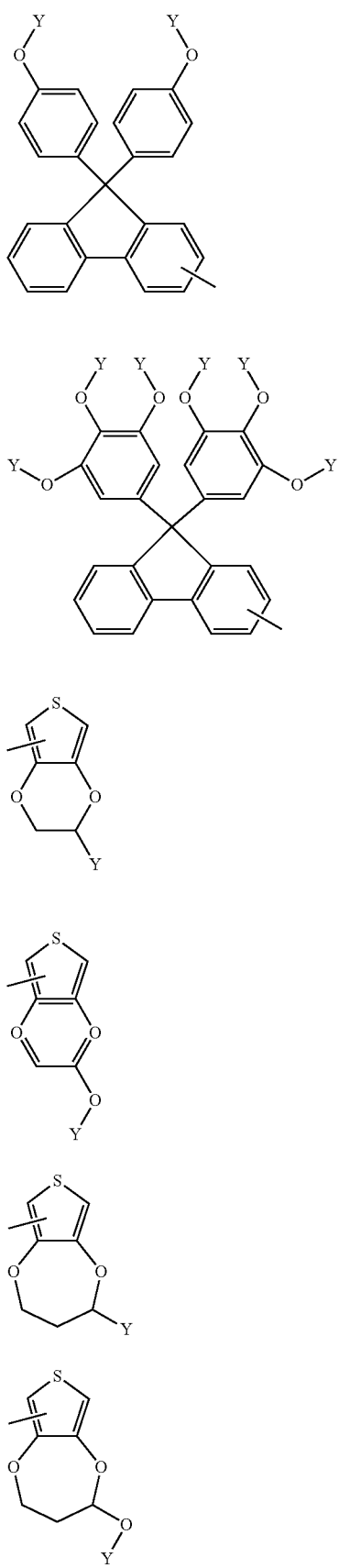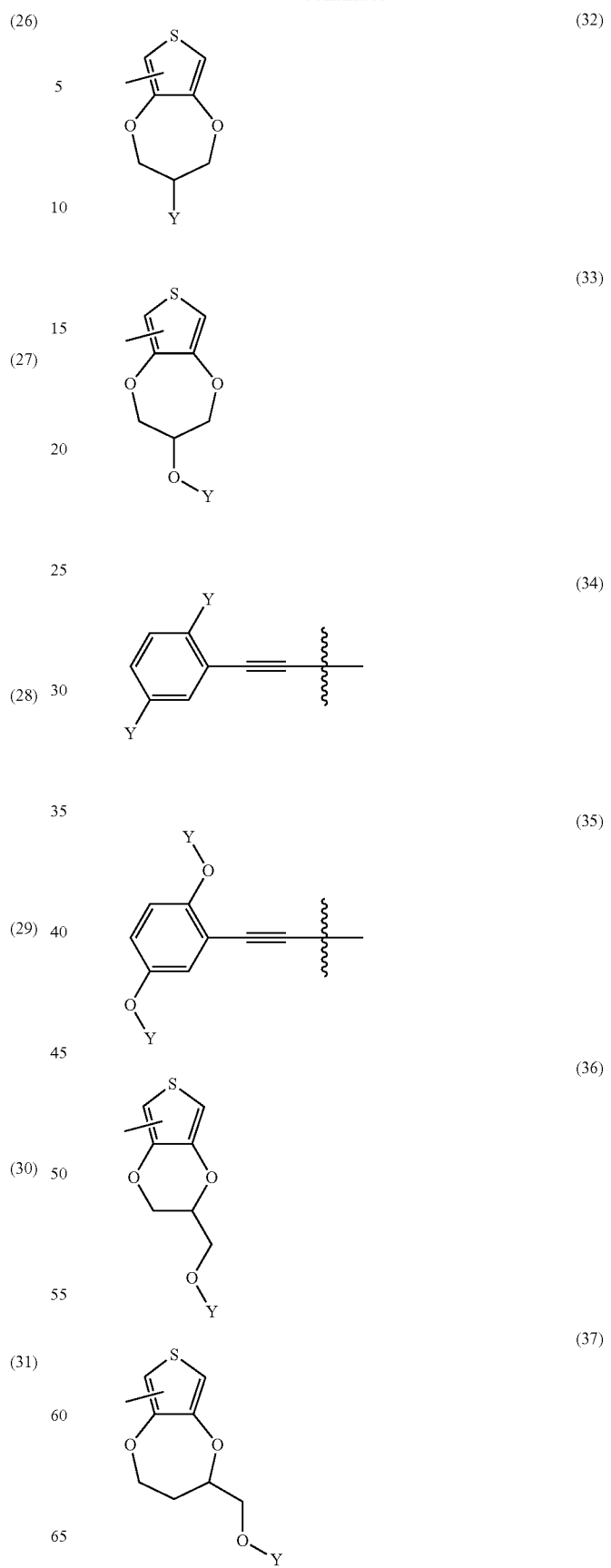

-continued

(38)
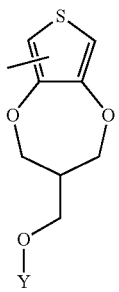

In each compound selected from the Compound Group 2a, independently;

all Ys are —$C_nH_{2n}$—$P^-Q^+$ (n is an integer between 1 and 20, $P^-$ is any one selected from the group consisting of $SO_3^-$, $PO_3^{2-}$ and $CO_2^-$, $Q^+$ is any one selected from the group consisting of $H^+$, $Li^+$. $Na^+$, $K^+$, $Rb^+$, $Cs^+$, $N^+H_4$, and $N^+R_1R_2R_3R_4$, $R_1$, $R_2$, $R_3$ and $R_4$ are each independently any one selected from C1 to C11 alkyl groups), or at least one of Ys is —$C_nH_{2n}$—$P^-$ (n is an integer between 1 and 20, $P^-$ is any one selected from the group consisting of $SO_3^-$, $PO_3^{2-}$ and $CO_2^-$), and the rest of Ys is —$C_nH_{2n}$—$P^-Q^+$ (n is an integer between 1 and 20, $P^-$ is any one selected from the group consisting of $SO_3^-$, $PO_3^{2-}$, and $CO_2^-$, $Q^+$ is any one selected from the group consisting of $H^+$, $Li^+$. $Na^+$, $K^+$, $Rb^+$, $Cs^+$, $N^+H_4$, and $N^+R_1R_2R_3R_4$, and $R_1$, $R_2$, $R_3$ and $R_4$ are each independently any one selected from C1 to C11 alkyl groups).

<Compound Group 2b>

(01)
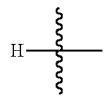

(02)
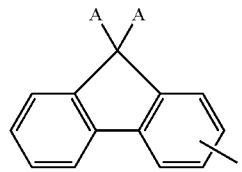

(03)
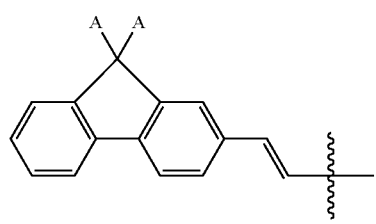

(04)
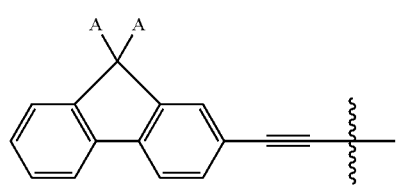

-continued

(05)
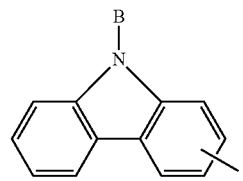

(06)
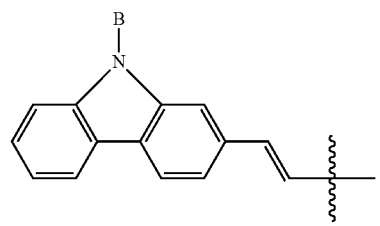

(07)
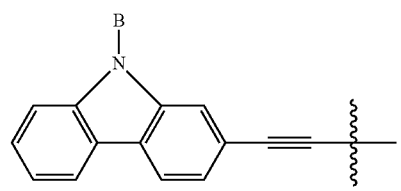

(08)

(09)
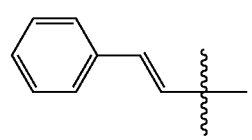

(10)
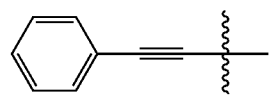

(11)
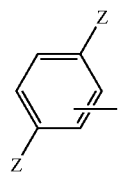

(12)
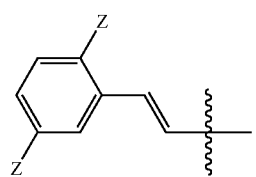

(13)
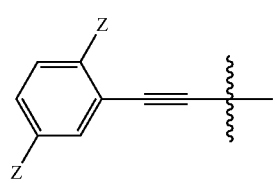

(14)
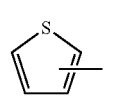

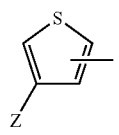 (15)
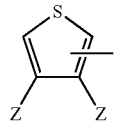 (16)
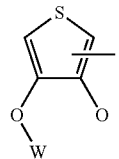 (17)
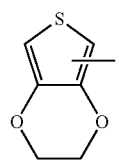 (18)
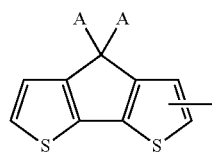 (19)
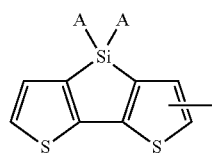 (20)
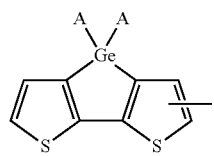 (21)
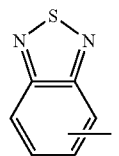 (22)
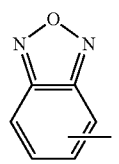 (23)
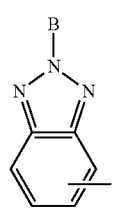 (24)
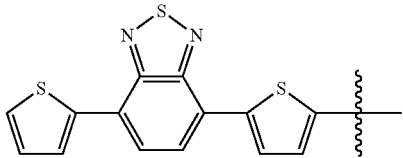 (25)
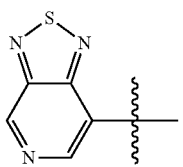 (26)
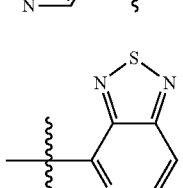 (27)
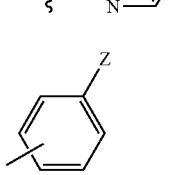 (28)
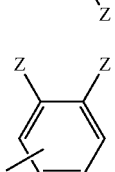 (29)
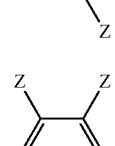 (30)
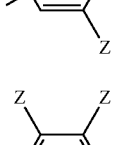 (31)
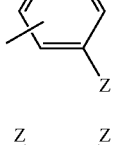 (32)
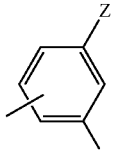 (33)

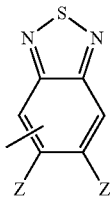
(34)

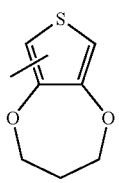
(35)

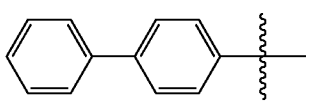
(36)

In the Compound Group 2b, A is each independently any one selected from the group consisting of —H, —NR$_2$, —NH$_2$, —OH, —OR, —NHC(=O)R, —OC(=O)R, —R, —CH=CR$_2$, F, Cl, Br, and I, B is each independently any one selected from the group consisting of —H, —R, —CH=CR$_2$, F, Cl, Br, and I, Z is each independently any one selected from the group consisting of —NR$_2$, —NH$_2$, —OH, —OR, —NHC(=O)R, —OC(=O)R, —R, —CH=CR$_2$, F, Cl, Br, I, —C(=O)R, —C(=O)OR, and —C(=O)NR$_1$R$_2$, W is each independently any one selected from —H and —R, and R, R$_2$, R$_3$ and R$_4$ are each independently any one selected from C1 to C20 alkyl groups.

The p-doped conjugated small molecular electrolyte may have an oxidized portion in a main chain (backbone) and a charge at a side chain, and a charge opposite to the charge which the side chain has, as a counter ion. Specifically, at least one of the side chains has any one anion selected from the group consisting of SO$_3^-$, PO$_3^{2-}$ and CO$_2^-$, and the p-doped conjugated small molecular electrolyte may have additional side chains. The additional side chain may have any one anion selected from the group consisting of SO$_3^-$, PO$_3^{2-}$ and CO$_2^-$, and any one cation selected from the group consisting of H$^+$, Li$^+$, Na$^+$, K+, Rb$^+$, Cs$^+$, N$^+$H$_4$, and N$^+$R$_1$R$_2$R$_3$R$_4$ as a counter ion. Herein, R$_1$, R$_2$, R$_3$ and R$_4$ are each independently any one selected from C1 to C11 alkyl groups.

Further, the p-doped conjugated small molecular electrolyte may comprise an electron donating group. The "electron donating group" refers to substituted or unsubstituted C1-C24 alkyl, alkoxy, thioalkoxy, amine group, imine group, carboxylic group, phosphate group, sulfonate group, or a combination thereof, and, for the chemical species, the expression "substituted" means to be substituted with a group that does not interfere in the preferable products or methods, for example, such substituents may include alkyl, alkoxy and the like.

Specifically, the electron donating group may be any one selected from the group consisting of —NR$_2$, —NH$_2$, —OH, —OR, —NHC(=O)R, —OC(=O)R, —R, —CH=CH$_2$ and —CH=CR$_2$, but are not limited thereto. These electron donating groups expect a role to enrich electron density of a main chain of the conjugated small molecule by providing with electrons thereto.

Further, the p-doped conjugated small molecular electrolyte may comprise an electron withdrawing group. Examples of the electron withdrawing group may include aryl, phenyl, halo (F, Cl, Br, I), —C(=O)R, —C(=O)OR, —C(=O)NR$_1$R$_2$(R, R$_1$ and R$_2$ are independently H or C1-C20 alkyl.), and the like, but are not limited thereto. These electron withdrawing groups expect a role to reduce electron density of a main chain of the conjugated small molecule by receiving electrons therefrom.

By appropriate combination of functional groups comprised in these electron donating groups and electron withdrawing groups, the doped state of the p-doped conjugated small molecular electrolyte can be adjusted so that the change in the work function is finely controlled.

Therefore, the p-doped conjugated small molecular electrolyte of the present disclosure is a doped form with lack of one electron in the main chain and has the structure combined with an anion functional group. The p-doped conjugated small molecular electrolyte can be easily prepared by oxidation reaction of a conjugated polyelectrolyte comprising a compound represented by Formula 4.

[Ar$_4$—Ar$_3$—Ar$_4$]$^+$  <Formula 4>

In Formula 4, Ar$_3$ is any one selected from the following Compound Group 3, and Ar$_4$ is any one selected from the following Compound Group 4 or the following Compound Group 2b.

<Compound Group 3>

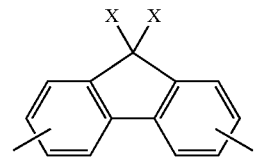
(01)

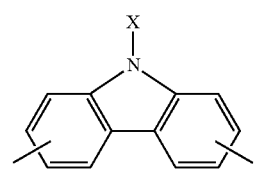
(02)

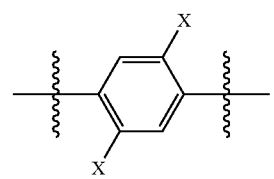
(03)

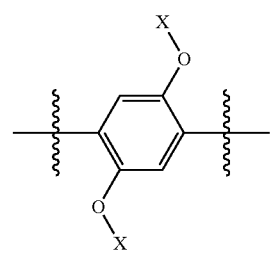
(04)

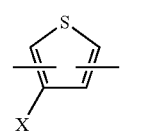
(05)

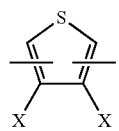 (06)
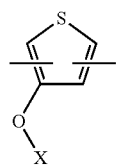 (07)
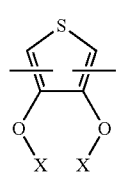 (08)
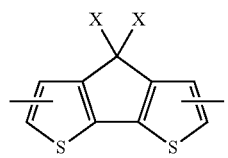 (09)
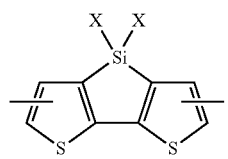 (10)
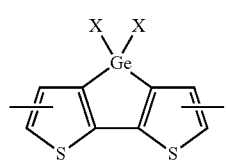 (11)
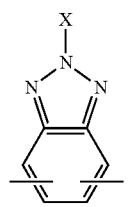 (12)
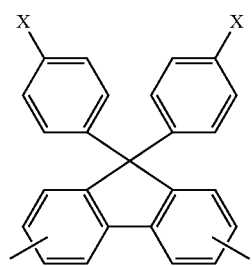 (13)
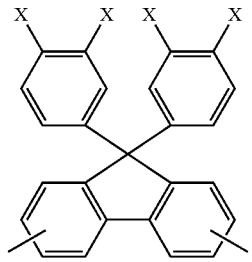 (14)
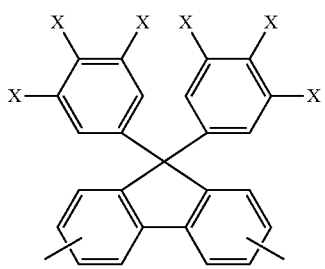 (15)
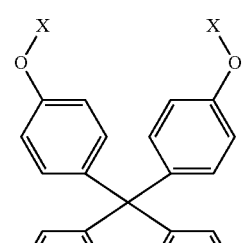 (16)
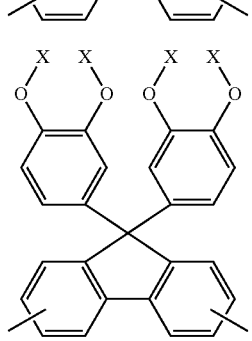 (17)
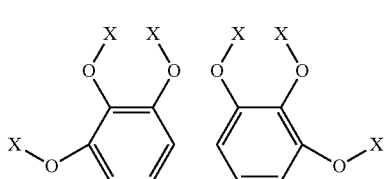 (18)
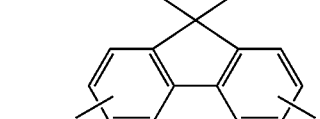
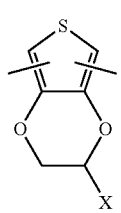 (19)

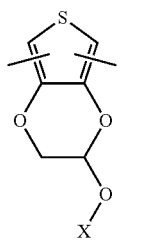
(20)

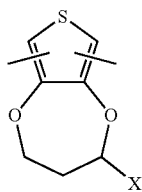
(21)

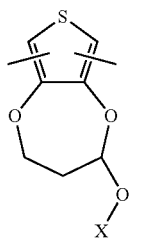
(22)

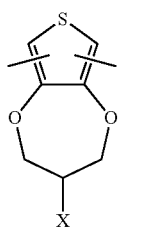
(23)

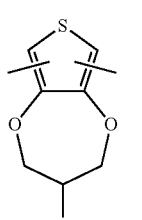
(24)

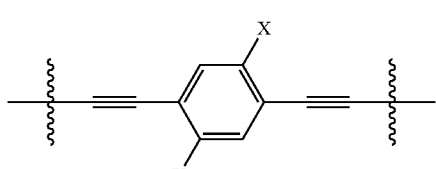
(25)

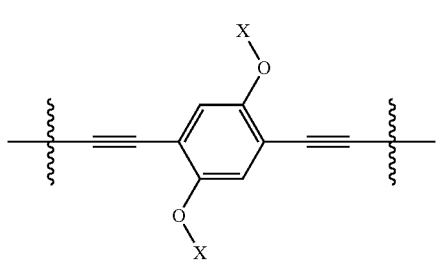
(26)

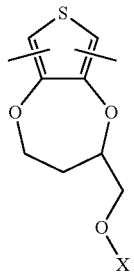
(27)

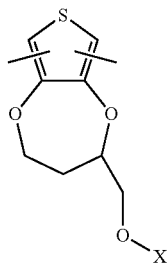
(28)

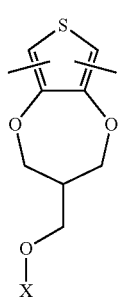
(29)

wherein, in the Compound Group 3, X is each independently $-C_nH_{2n}-P^-Q^+$ (n is an integer between 1 and 20), $P^-$ is any one selected from the group consisting of $SO_3^-$, $PO_3^{2-}$, and $CO_2^-$, $Q^+$ is any one selected from the group consisting of $H^+$, $Li^+$, $Na^+$, $K^+$, $Rb^+$, $Cs^+$, $N^+H_4$, and $N^+R_1R_2R_3R_4$, and $R_1$, $R_2$, $R_3$ and $R_4$ are each independently any one selected from C1 to C11 alkyl groups.

<Compound Group 4>

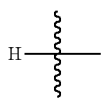
(01)

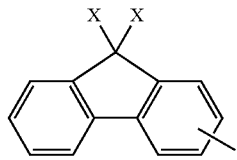
(02)

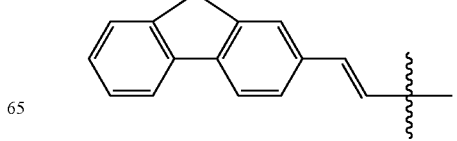
(03)

-continued
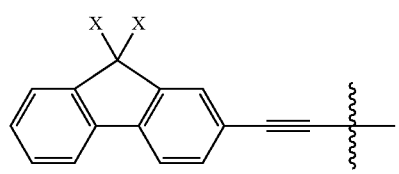 (04)
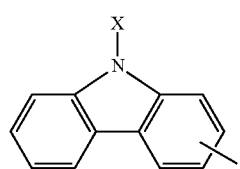 (05)
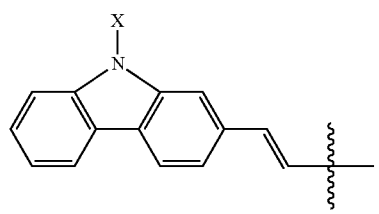 (06)
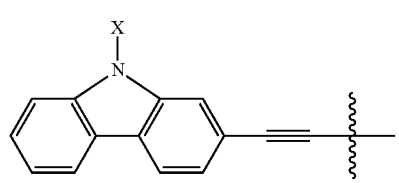 (07)
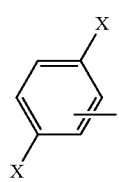 (08)
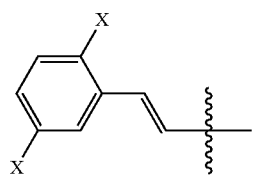 (09)
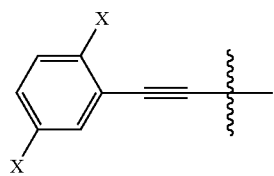 (10)
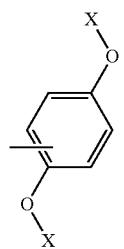 (11)
-continued
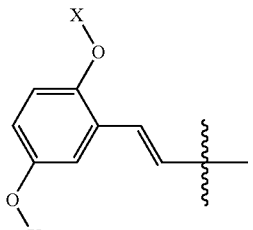 (12)
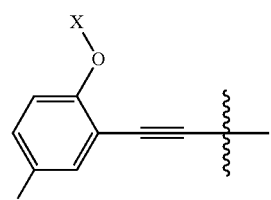 (13)
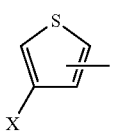 (14)
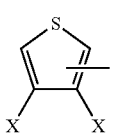 (15)
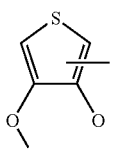 (16)
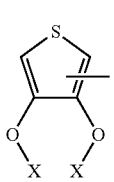 (17)
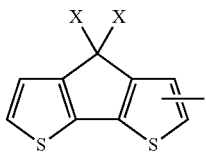 (18)
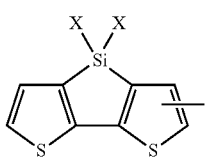 (19)
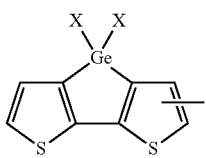 (20)

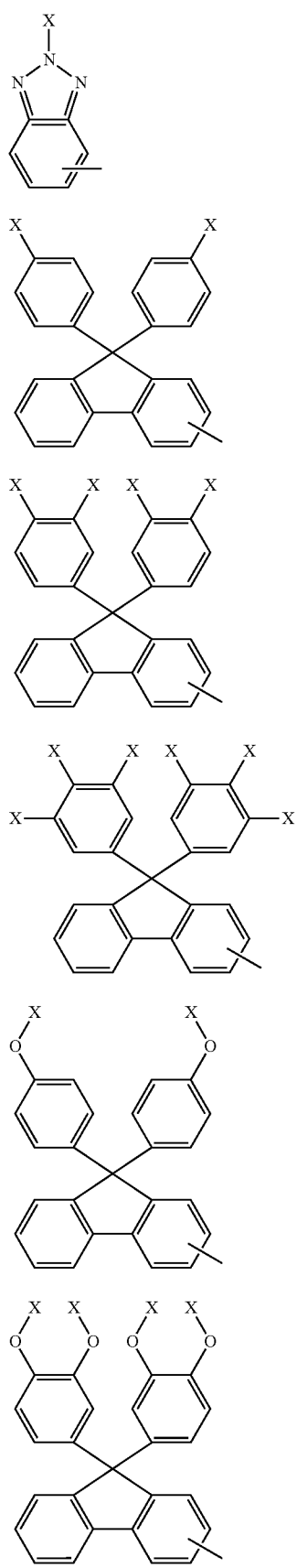
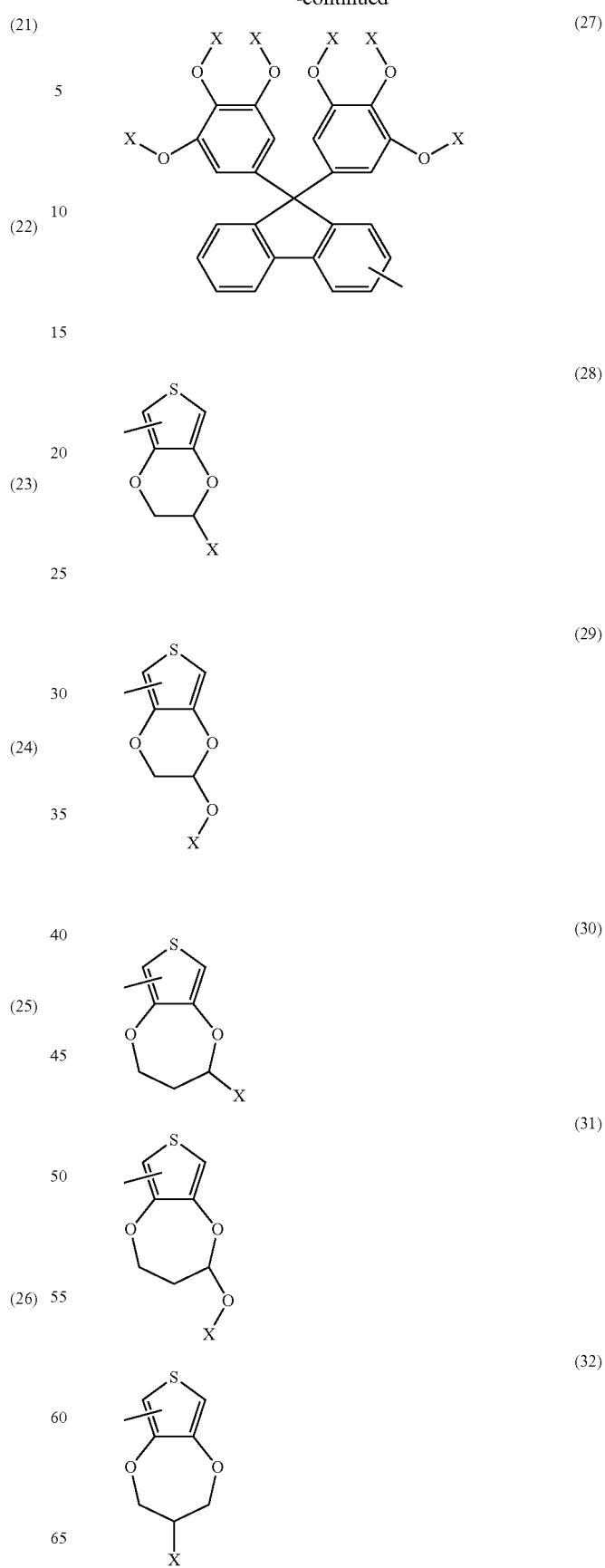

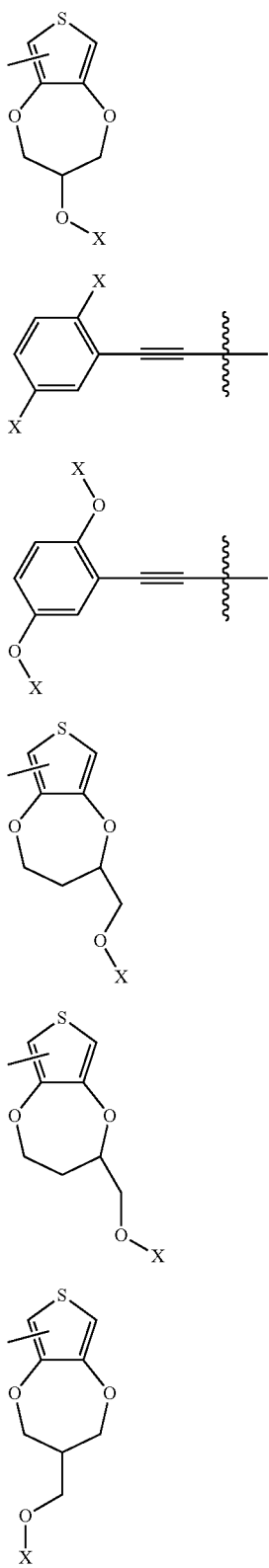

In each compound selected from the Compound Group 4, X is each independently —$C_nH_{2n}$—$P^-Q^+$ (n is an integer between 1 and 20), $P^-$ is any one selected from the group consisting of $SO_3^-$, $PO_3^{2-}$, and $CO_2^-$, $Q^+$ is any one selected from the group consisting of $H^+$, $Li^+$, $Na^+$, $K^+$, $Rb^+$, $Cs^+$, $N^+H_4$, and $N^+R_1R_2R_3R_4$, and $R_1$, $R_2$, $R_3$ and $R_4$ are each independently any one selected from C1 to C11 alkyl groups.

<Compound Group 2b>

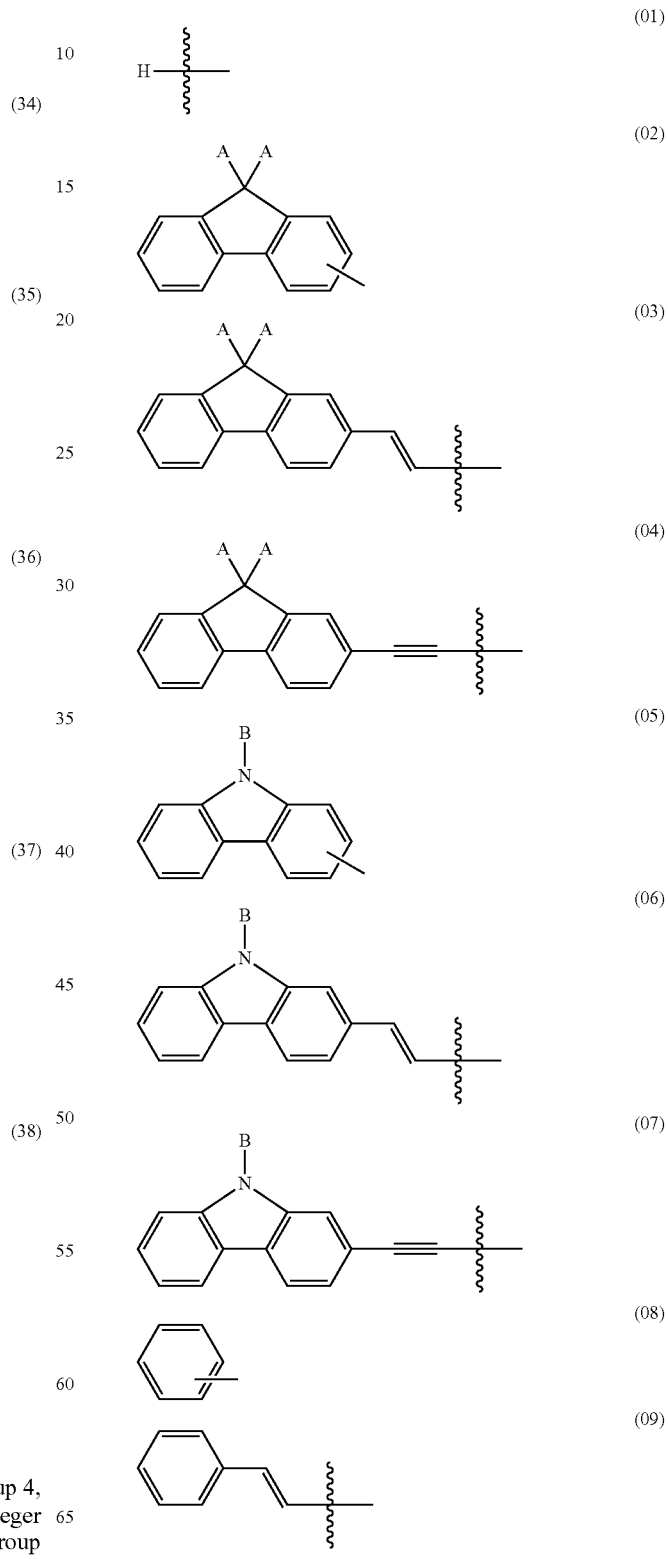

-continued
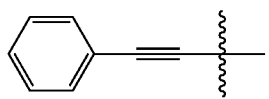 (10)
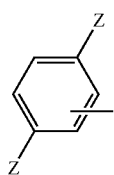 (11)
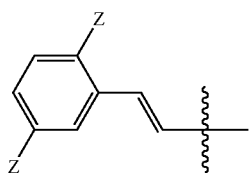 (12)
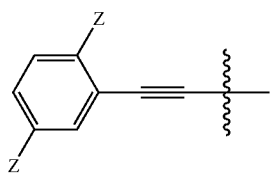 (13)
 (14)
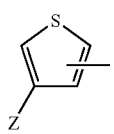 (15)
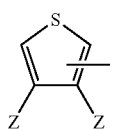 (16)
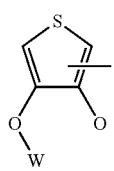 (17)
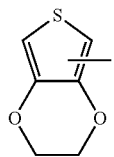 (18)
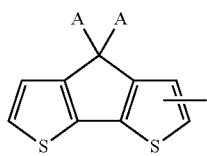 (19)
-continued
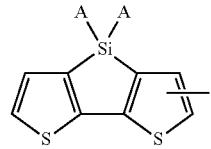 (20)
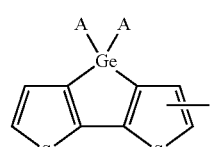 (21)
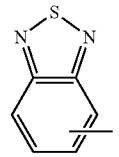 (22)
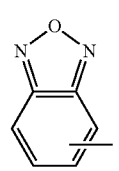 (23)
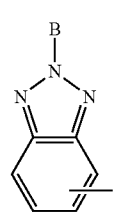 (24)
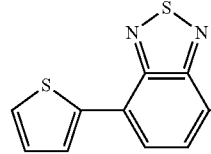 (25)
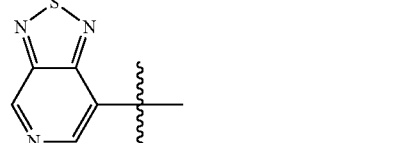 (26)
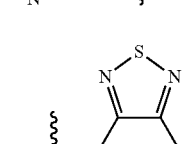 (27)
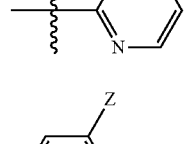 (28)
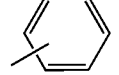

-continued

(29) 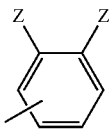

(30) 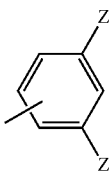

(31) 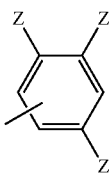

(32) 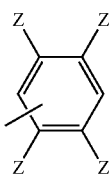

(33) 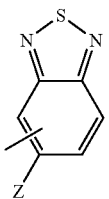

(34) 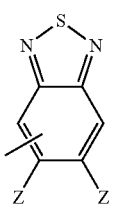

(35) 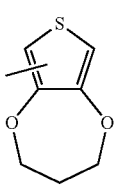

(36) 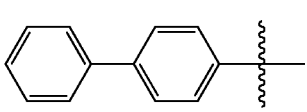

In the Compound Group 2b, A is each independently any one selected from the group consisting of —H, —NR$_2$, —NH$_2$, —OH, —OR, —NHC(=O)R, —OC(=O)R, —R, —CH=CR$_2$, F, Cl, Br, and I, B is each independently any one selected from the group consisting of —H, —R, —CH=CR$_2$, F, Cl, Br, and I, Z is each independently any one selected from the group consisting of —NR$_2$, —NH$_2$, —OH, —OR, —NHC(=O)R, —OC(=O)R, —R, —CH=CR$_2$, F, Cl, Br, I, —C(=O)R, —C(=O)OR, and —C(=O)NR$_1$R$_2$, W is each independently any one selected from —H and —R, and R, R$_2$, R$_3$ and R$_4$ are each independently any one selected from C1 to C20 alkyl groups.

The oxidation reaction of the conjugated small molecular electrolyte represented by Formula 4 is not particularly limited, and may be induced, for example, by adding an acid or an oxidizing agent to the conjugated polymer compound, or performing a coating of conjugated polyelectrolyte to form a polyelectrolyte layer and then using cyclovoltammetry (CV).

For example, diphenylfluorene (DPF-R), a kind of n-type conjugated small molecular electrolytes (n-CSEs), is treated with persulfate salts as an oxidizing agent to obtain p-doped conjugated small molecular electrolytes (p-CSEs). The reaction may be represented by Reaction Scheme 1a.

[Reaction Scheme 1a]

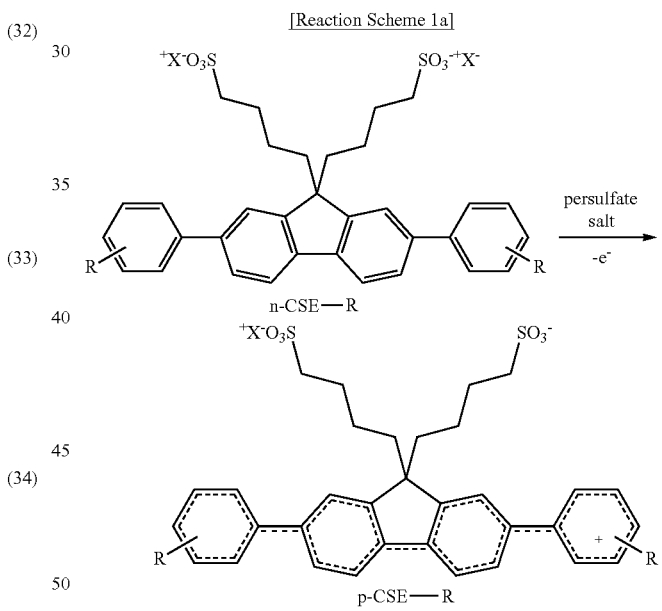

In Reaction Scheme 1a, X in SO$_3^-$X$^+$ may be Li, K, NH$_4$, or Na. Further, in Reaction Scheme 1a, the persulfate salt may be selected from the group consisting of XHSO$_5$ (where X=K); X$_2$S$_2$O$_8$ (where X=Na, K, Li, Rb, Cs or NH$_4$); XS$_2$O$_8$ (where X=Ba, Zn, Ca, Be, Mg, Sr, Ti or Fe); X$_2$(S$_2$O$_8$)$_3$ (where X=Sb, Al or V); X(S$_2$O$_8$)$_2$ (where X=Ti); and X$_2$(S$_2$O$_8$)$_5$ (where X=V), but is not limited thereto. Further, in Reaction Scheme 1a, each R may be independently a halogen group such as —F, —Cl, —Br and —I, or an electron donating group such as —OMe. However, the present disclosure is not limited thereto. For the sake of convenience, the p-doped conjugated small molecular electrolyte which is produced on right of Reaction Scheme 1a is to be referred to as p-DPF in the case of R=—H, p-DPF-F in the case of R=—F, and p-DPF-O in the case of R=—OMe (methoxy).

Their structures are shown in Formula 5.

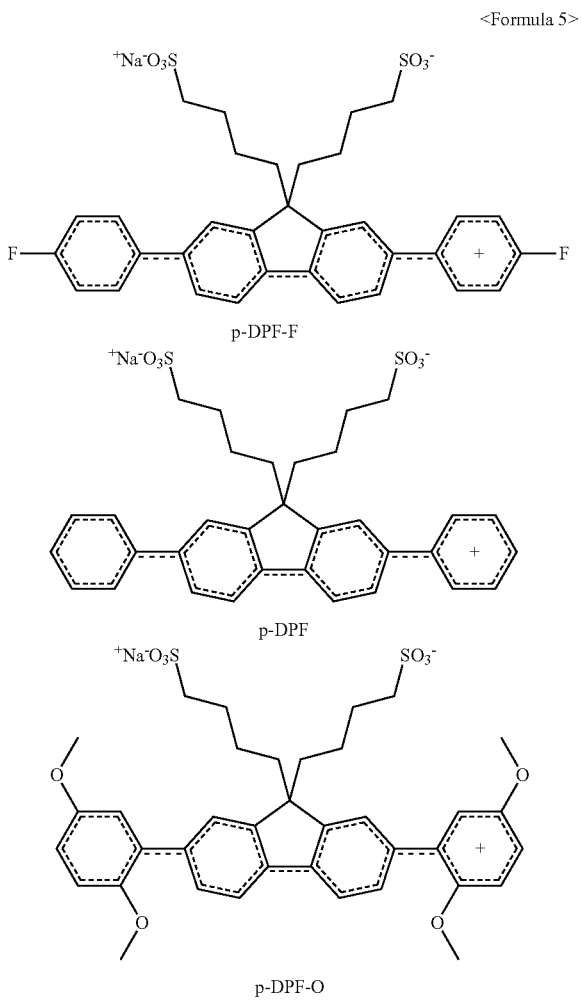

<Formula 5> p-DPF-F p-DPF p-DPF-O

In a preferred embodiment, the p-doped conjugated polyelectrolyte may be a compound represented by Formula 2a.

<Formula 2a>

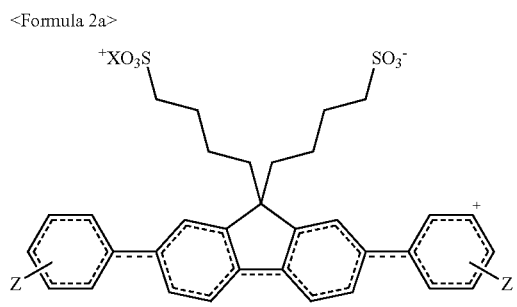

(where X is any one selected from the group consisting of Li, Na, K, Rb, Cs and NH$_4$, Z is any one selected from the group consisting of —NR$_2$, —NH$_2$, —OH, —OR, —NHC(=O)R, —OC(=O)R, —R, —CH=CR$_2$, F, Cl, Br, I, —C(=O)R, —C(=O)OR and —C(=O)NR$_1$R$_2$, and superscript "+" in the benzene ring indicates an oxidized portion of a main chain of the small molecule.)

A main chain of the conjugated small molecular electrolyte is oxidized to generate radical cation and forms an electrostatic coupling with sulfonic acid anion, where the coupling can be formed at 'intramolecular' or 'intermolecular'. Due to such structural characteristics, it generates a dipole pointing toward the opposite direction to that of n-type conjugated small molecular electrolyte. As a result, it can effectively act as a hole transport layer between metal electrode and organic materials.

Meanwhile, for comparison of the performance with that of the CSEs of the present disclosure, poly(9,9-bis(4'-sulfonatobutyl)fluorene-alt-co-1,4-phenylene) (PFP), a kind of n-type conjugated polyelectrolyte (n-CPEs), is treated with persulfate salts as an oxidizing agent to obtain p-doped conjugated polyelectrolyte (p-CPEs). The reaction may be represented by Reaction Scheme 1b.

[Reaction Scheme 1b]

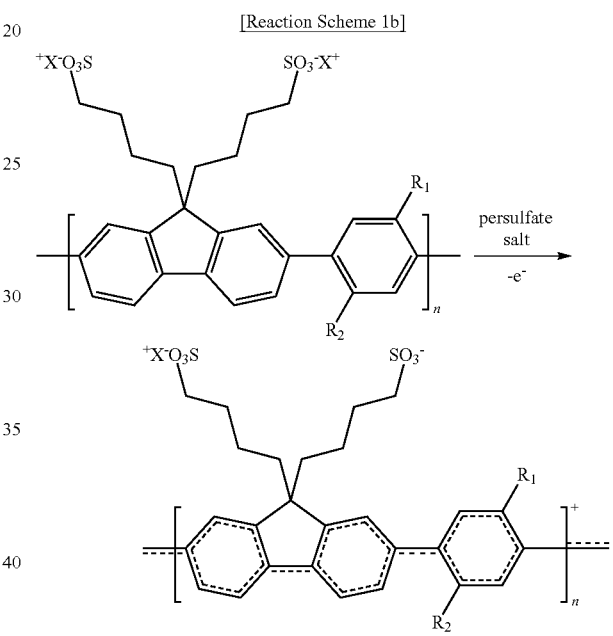

In Reaction Scheme 1b, X in SO$_3^-$X$^+$ may be Li, K, NH$_4$, or Na. Further, in Reaction Scheme 1b, the persulfate salt may be selected from the group consisting of XHSO$_5$ (where X=K); X$_2$S$_2$O$_8$ (where X=Na, K, Li, Rb, Cs or NH$_4$); XS$_2$O$_8$ (where X=Ba, Zn, Ca, Be, Mg, Sr, Ti or Fe); X$_2$(S$_2$O$_8$)$_3$ (where X=Sb, Al or V); X(S$_2$O$_8$)$_2$ (where X=Ti); and X$_2$(S$_2$O$_8$)$_5$ (where X=V), but is not limited thereto. Further, in Reaction Scheme 1b, R$_1$ and R$_2$ may be each independently a halogen group such as —F, —Cl, —Br and —I, or an electron donating group such as —OMe. However, the present disclosure is not limited thereto. For the sake of convenience, the p-doped p-doped conjugated polyelectrolyte which is produced on right of Reaction Scheme 1b is to be referred to as p-PFP in the case of R$_1$=—H and R$_2$=—H, p-PFP-F in the case of R$_1$=—H and R$_2$=—F, p-PFP-OMe in the case of R$_1$=—H and R$_2$=—OMe (methoxy), and p-PFP-O in the case of R$_1$=—OMe and R$_2$=—OMe.

In a preferred embodiment, the p-doped conjugated polyelectrolyte may be a compound represented by Formula 2b.

<Formula 2b>

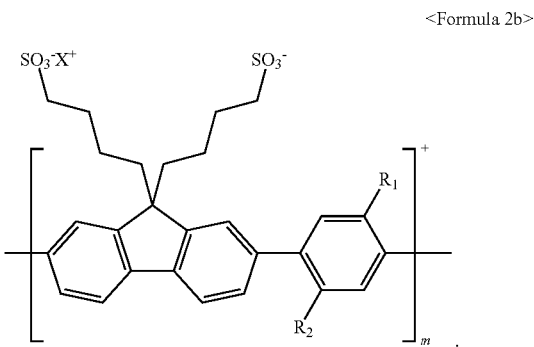

(where X is any one selected from the group consisting of Li, Na, K, Rb, Cs and $NH_4$, superscript "+" in the square bracket indicates an oxidized portion of a main chain of the polymer, and m represents an integer between 1 and 1,000,000.)

FIG. 1 is a schematic view illustrating an organic electronic device 100 according to an embodiment of the present disclosure.

Referring to FIG. 1, a first electrode 120, a p-doped conjugated small molecular electrolyte layer 130, an organic active layer 140, an electron transport layer 150, and a second electrode 160 may be sequentially formed on a substrate 110. Herein, the electron transport layer 150 may be omitted.

The substrate 110 is used to support the organic electronic device, and may be a light transmitting inorganic substrate selected from glass, quartz, $Al_2O_3$, and SiC, or a light transmitting plastic substrate selected from PET (polyethylene terephthalate), PES (polyethersulfone), PS (polystyrene), PC (polycarbonate), PI (polyimide), PEN (polyethylene naphthalate), and PAR (polyarylate).

The first electrode 120 may be a light transmitting electrode. The first electrode 120 may be an ITO (Indium Tin Oxide) film, an FTO (Fluorinated Tin Oxide) film, an IZO (Indium Zinc Oxide) film, an AZO (Al-doped Zinc Oxide) film, a ZnO (Zinc Oxide) film, or an IZTO (Indium Zinc Tin Oxide) film.

The p-doped conjugated small molecular electrolyte layer 130 exhibits characteristics of electrolyte by being provided with a conjugated small molecular having a charge at a side chain and an oxidized portion in a main chain, and a charge opposite to the charge which the side chain has, as a counter ion.

Specifically, the side chain may have any one anion selected from the group consisting of $SO_3^-$, $PO_3^{2-}$ and $CO_2^-$, and any one cation selected from the group consisting of $H^+$, $Li^+$, $Na^+$, $K^+$, $Rb^+$, $Cs^+$, $N^+H_4$, and $N^+R_1R_2R_3R_4$, as a counter ion (where $R_1$, $R_2$, $R_3$, and $R_4$ are each independently any one selected from C1-C11 alkyl groups).

The p-doped conjugated small molecular electrolyte layer 130 may function as a hole transport layer to easily transport holes supplied via an external circuit from the first electrode 120 to the organic active layer 140 (in the case of organic light emitting devices), or to easily transport holes generated in the organic active layer 140 to the first electrode 120 (in the case of organic solar cells). Together with this, the p-doped polyelectrolyte layer 130 may function as a buffer layer to alleviate surface roughness of the first electrode 120. Also, since a lowest unoccupied molecular orbital (LUMO) level of the p-doped conjugated small molecular electrolyte layer 130 is higher than the LUMO level of the organic active layer 140, the p-doped conjugated small molecular electrolyte layer 130 may function as an electron stop layer to block electrons from being introduced into the first electrode 120 from the organic active layer 140.

The p-doped conjugated small molecular electrolyte 130 may contain a compound represented by Formula 1.

In a preferred embodiment, the p-doped conjugated small molecular electrolyte layer 130 may contain a compound represented by Formula 2a.

The organic active layer 140 may be a light emitting layer or a photoelectric conversion layer. Herein, the light emitting layer means a layer generating light by combination of electrons and holes supplied from an outside, and the photoelectric conversion layer means a layer where electron-hole pairs (excitons) are generated by external light and separation into respective charges occurs. In the case of constituting the organic active layer as the light emitting layer or the photoelectric conversion layer, the organic electronic device 100 may be fabricated into an organic light emitting device or an organic solar cell.

The material of the light emitting layer and the photoelectric conversion layer is not particularly limited, and various polymers or low molecular weight organic materials may be used.

For example, the material of the light emitting layer may be selected from polyaniline, polypyrrole, polyacetylene, poly(3,4-ethylenedioxythiophene) (PEDOT), polyphenylenevinylene (PPV), polyfluorene, polyparaphenylene (PPP), polyalkylthiophene, polypyridine (PPy), polyvinylcarbazole, or copolymers thereof, or may be selected from appropriate host/dopant materials.

For example, the material of an electron donor material in the photoelectric conversion layer may be polythiophene, polyfluorene, polyaniline, polycarbazole, polyvinylcarbazole, polyphenylene, polyphenylvinylene, polysilane, polyisothianaphthanene, polythiazole, polybenzothiazole, polythiopheneoxide, or copolymers thereof. In an example, the electron donor material may be one of polythiophenes, such as poly(3-hexylthiophene (P3HT), or may be a copolymer of the above polymers, such as PCPDTBT (poly[2,6-(4,4-bis-(2-ethylhexyl)-4H-cyclopenta[2,1-b;  3,4-b']dithiophene)-alt-4,7-(2,1,3-benzothiadiazole)], PCDTBT (poly[N-9''-heptadecanyl-2,7-carbazole-alt-5,5-(4',7'-di-2-thienyl-2',1',3'-benzothiadiazole)]), or PFDTBT (poly(2,7-(9-(2'-ethylhexyl)-9-hexyl-fluorene)-alt-5,5-(4',7'-di-2-thienyl-2', 1',3'-benzothiadiazole))). Also, for example, the electron acceptor material of the photoelectric conversion layer may be $C_{60}$ to $C_{84}$ fullerenes or derivatives thereof, perylenes, polymers or quantum dots. The fullerene derivatives may be PCBM, for example, $PCBM(C_{60})$([6,6]-phenyl-$C_{61}$-butyric acid methyl ester) or $PCBM(C_{70})$([6,6]-phenyl-$C_{71}$-butyric acid methyl ester).

The electron transport layer 150 may play a role to easily transport electrons supplied via an external circuit from the second electrode 160 to the organic active layer 140 (in the case of organic light emitting devices), or to easily transport electrons generated in the organic active layer 140 to the second electrode 160 (in the case of organic solar cells). Together with this, the electron transport layer 150 may play a role as a hole stop layer to block holes generated in the organic active layer 140 from being introduced into the second electrode 160. Exemplary electron transport layer 150 may be a titanium oxide layer. The titanium oxide layer may prevent degradation of devices due to permeation of oxygen or vapor into the organic active layer 140, and may play a role as an optical spacer to increase the amount of light introduced into the organic active layer 140 and also as a life-cycle increasing layer to increase life-cycle of the organic electronic devices. The titanium oxide layer may be formed by using a sol-gel method.

The second electrode 160 may be a metal or a conductive polyelectrode having a lower work function than the first electrode 120. In an example, the second electrode 160 may be any one metal electrode selected from the group consisting of Li, Mg, Ca, Ba, Al, Cu, Ag, Au, W, Ni, Zn, Ti, Zr, Hf, Cd, Pd, Cs, and alloys thereof. In case the second electrode 160 is metal electrode, the second electrode 160 may be formed by a thermal vapor deposition, an electronic beam deposition, a sputtering, or a chemical deposition, or by coating a metal-containing paste for formation of electrodes and thermally annealing the coated paste. However, the present disclosure is not limited thereto.

Hereinafter, to help the understanding of the present disclosure, preferred examples will be provided. It will be understood that the following examples are not provided to limit the present disclosure but are only provided to help the understanding of the present disclosure.

EXAMPLES

Synthetic Example 1

Synthesis of Conjugated Small Molecular Electrolytes (CSEs)

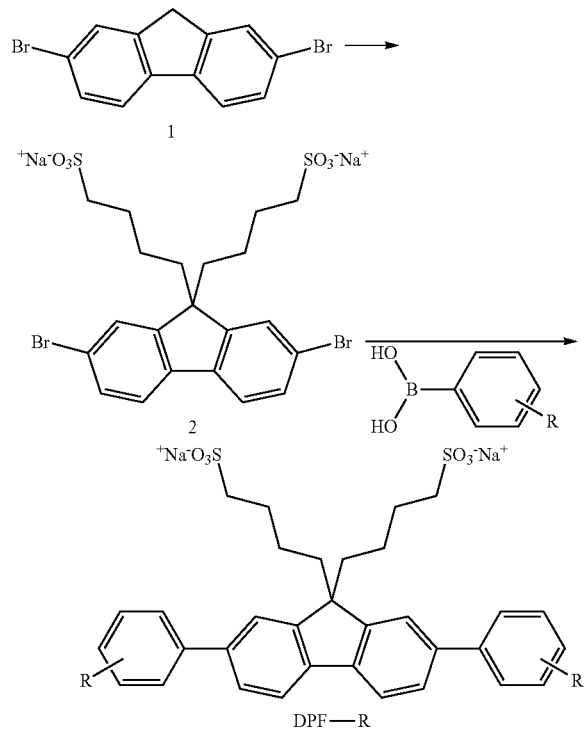

Synthesis Example 1-1

Synthesis of Intermediate

To a solution of 2,7-dibromo-9H-fluorene (2.0 g, 15.4 mmol) and small amount of triethylbenzylammonium chloride in 30 mL of DMSO, NaOH aqueous solution ($H_2O$ (4 mL)+NaOH (2.0 g, 50.0 mmol)) was added. After stirring for 30 min, 1,4-butane sultone (2.1 g, 15.4 mmol) was added to the reaction mixture. The resulting mixture was vigorously stirred at 100° C. for 12 hours under argon gas. After the reaction mixture was cooled to room temperature, the solution was mixed with 100 mL of acetone. The precipitate was filtrated and washed with acetone, affording a pale yellow solid of monomer, sodium 4-(2,7-dibromo-9-(4-sulfonatobutyl)-9H-fluoren-9-yl)butyl sulfate (80-90% yield).

NMR chemical shift of the monomer obtained was as follows.

$^1$H NMR (400 MHz, DMSO-$d_6$, $\delta_{ppm}$): 7.73-7.71 (d, 2H, J=8.00 Hz), 7.66-7.65 (d, 2H, J=1.70 Hz), 7.47-7.44 (dd, 2H, J=8.00 Hz, J=1.70 Hz), 2.10-2.05 (m, 4H), 2.00-1.95 (m, 4H), 1.31-1.23 (m, 4H), 0.40-0.30 (m, 4H).

Synthesis Example 1-2

Synthesis of n-Type CSEs

The monomer obtained (1.28 g, 2.0 mmol) and a boronic ester derivative of phenylboronic acid or (2,5-dimethoxyphenyl)boronic acid (2.0 mmol), were dissolved in 54 mL of DMF/0.2M $NaCO_3$ (aq) (4/5, v/v). The resulting solution was deoxygenated with argon for 15 minutes. Then $Pd(OAc)_2$ (22.5 mg, 0.05 mol %) was added to the stirred solution under argon gas. The reaction mixture was then heated up to 100° C. and stirred for 12 hours. The viscous solution was then mixed with 300 mL of acetone. The precipitate was purified by column chromatography under methanol eluent. After dialysis, the water was removed by the low temperature drying method. The water-soluble DPFs were obtained respectively as a pale yellow solid (DPF) and a pale orange solid (DPF-O) in 70-80% yield.

NMR chemical shift of each material was as follows.

DPF. $^1$H NMR (300 MHz; $CD_3OD$, $\delta_{ppm}$): 7.83 (d, 2H), 7.72-7.67 (m, 6H), 7.64 (d, 2H), 7.45 (t, 4H), 7.34 (t, 2H), 2.54 (m, 4H), 2.20 (m, 4H), 1.60 (m, 4H), 0.78 (m, 4H).

DPF-O. $^1$H NMR (600 MHz, DMSO-$d_6$, $\delta_{ppm}$): 7.77 (d, 2H), 7.51 (s, 2H), 7.47 (d, 2H), 7.03 (d, 2H), 6.95 (d, 2H), 6.88 (d, 2H), 3.80 (s, 6H), 3.75 (s, 6H), 2.57 (m, 4H), 2.12 (m, 4H), 1.62 (m, 4H), 0.82 (m, 4H).

Synthesis Example 1-3

Synthesis of p-Type CSEs 0.005 g of the CSE obtained in above, i.e., DPF or DPF-O, in 1.0 mL of water was mixed with 3.0 mol of $(NH_4)_2S_2O_8$ as an oxidizing agent in 1.0 mL of water, followed by stirring at room temperature for 12 hours. The pale pink precipitate (p-DPF) and the pale brown precipitate (p-DPF-O) were collected, filtered under vacuum, and then washed with 100 mL of cold deionized water. The product was dried in hood overnight to obtain p-doped CSEs (p-DPF or p-DPF-O) in 90-100% yield.

NMR chemical shift of each material was as follows.

p-DPF. $^1$H NMR (300 MHz; $CD_3OD$, $\delta_{ppm}$): 7.83 (d, 2H), 7.70-7.67 (m, 6H), 7.63 (d, 2H), 7.46 (t, 4H), 7.33 (t, 2H), 2.55 (m, 4H), 2.20 (m, 4H), 1.59 (m, 4H), 0.76 (m, 4H).

p-DPF-O. $^1$H NMR (600 MHz, DMSO-$d_6$, $\delta_{ppm}$): 7.778 (d, 2H), 7.56 (s, 2H), 7.47 (d, 2H), 7.03 (d, 2H), 6.95 (d, 2H), 6.90 (d, 2H), 3.81 (s, 6H), 3.75 (s, 6H), 2.55 (m, 4H), 2.08 (m, 4H), 1.58 (m, 4H), 0.80 (m, 4H).

Synthetic Example 2

Synthesis of Conjugated Polyelectrolytes (CPEs)

[Reaction Scheme 3]

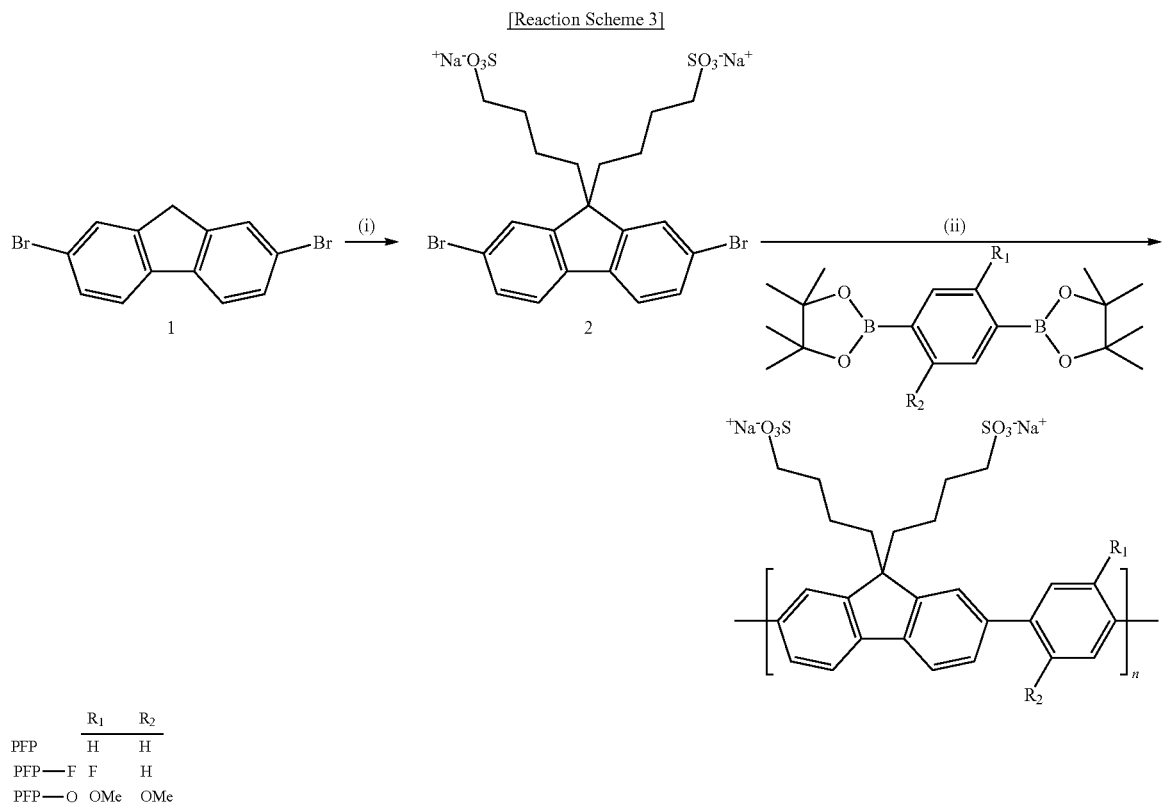

|  | R$_1$ | R$_2$ |
|---|---|---|
| PFP | H | H |
| PFP—F | F | H |
| PFP—O | OMe | OMe |

Synthesis Example 2-1

Synthesis of Intermediate (Monomer)

To a solution of 2,7-dibromo-9H-fluorene (2.0 g, 15.4 mmol) and small amount of triethylbenzylammonium chloride in 30 mL of DMSO, NaOH aqueous solution (H$_2$O (4 mL)+NaOH (2.0 g, 50.0 mmol)) was added. After stirring for 30 min, 1,4-butane sultone (2.1 g, 15.4 mmol) was added to the reaction mixture. The resulting mixture was vigorously stirred at 100° C. for 12 hours under argon gas. After the reaction mixture was cooled to room temperature, the solution was mixed with 100 mL of acetone. The precipitate was filtrated and washed with acetone, affording a pale yellow solid of monomer, sodium 4-(2,7-dibromo-9-(4-sulfonatobutyl)-9H-fluoren-9-yl)butyl sulfate (80-90% yield).

NMR chemical shift of the monomer obtained was as follows.

$^1$H NMR (400 MHz, DMSO-d$_6$, $\delta_{ppm}$): 7.73-7.71 (d, 2H, J=8.00 Hz), 7.66-7.65 (d, 2H, J=1.70 Hz), 7.47-7.44 (dd, 2H, J=8.00 Hz, J=1.70 Hz), 2.10-2.05 (m, 4H), 2.00-1.95 (m, 4H), 1.31-1.23 (m, 4H), 0.40-0.30 (m, 4H).

Synthesis Example 2-2

Synthesis of n-Type CSEs Via Polymerization of Monomer

The monomer obtained (1.28 g, 2.0 mmol) and a boronic ester derivative (1,4-bis(4,4,5,5-tetramethyl-1,3,2-dioxaborolan-2-yl)benzene, 2,2'-(2-fluoro-1,4-phenylene)bis(4,4,5,5-tetramethyl-1,3,2-dioxaborolane), or 2,2'-(2,5-dimethoxy-1,4-phenylene)bis(4,4,5,5,-tetramethyl-1,3,2-dioxaborolane)) (2.0 mmol) were dissolved in 54 mL of DMF/0.2M NaCO$_3$ (aq) (4/5, v/v). The resulting solution was deoxygenated with argon for 15 minutes. Then Pd(OAc)$_2$ (22.5 mg, 0.05 mol %) was added to the stirred solution under argon gas. The reaction mixture was then heated up to 100° C. and stirred for 12 hours. The viscous solution was then mixed with 300 mL of acetone. The precipitate was dissolved in water and purified through dialysis using 12 kD molecular-weight-cutoff (MWCO) regenerated cellulose membranes. After dialysis, the water was removed by the low temperature drying method. The water-soluble CPFs were obtained respectively as a pale yellow solid (PFP), a pale orange solid (PFP-F) and a pale pink solid (PFP-O) in 40% yield.

NMR chemical shift of each material was as follows.

PFP. $^1$H NMR (400 MHz; DMSO-d$_6$, $\delta_{ppm}$): 7.97-7.36 (m, 10H), 2.33-2.08 (m, 8H), 1.42 (br, 4H), 0.69 (br, 4H).

PFP-F. $^1$H NMR (600 MHz, DMSO-d$_6$, $\delta_{ppm}$): 8.30-7.19 (m, 9H), 2.28 (br, 4H), 2.13 (br, 4H), 1.43 (br, 4H), 0.69 (br, 4H); $^{13}$C NMR (150 MHz, DMSO-d$_6$, $\delta_{ppm}$): 163.7, 160.6, 158.9, 151.5, 150.9, 143.0, 141.8, 140.1, 139.9, 137.8, 134.0, 131.3, 128.0, 127.2, 125.9, 125.0, 123.4, 121.2, 116.1, 116.0, 114.3, 114.2, 55.2, 55.0, 54.8, 51.4, 34.5, 25.5, 23.2.

PFP-O. $^1$H NMR (600 MHz, DMSO-d$_6$, $\delta_{ppm}$): 8.28-6.90 (m, 8H), 2.30 (br, 4H), 2.02 (br, 4H), 1.43 (br, 4H), 0.76 (br, 4H); $^{13}$C NMR. (150 MHz, DMSO-d$_6$, $\delta_{ppm}$): 153.5, 151.1, 150.5, 150.4, 150.1, 150.0, 149.8, 139.1, 139.0, 136.9, 136.7, 131.2, 129.9, 128.0, 127.0, 124.2, 124.1, 119.5, 119.4, 116.0, 115.8, 114.8, 113.4, 113.3, 56.4, 56.2, 55.5, 55.4, 54.4, 51.3, 51.2, 34.3, 25.3, 23.2.

Synthesis Example 2-3

Synthesis of p-Type CPEs 0.005 g of the CPE obtained in above, i.e., PFP, PFP-F or PFP-O, in 1.0 mL of water was mixed with 3.0 mol of $X_2S_2O_8$ (where X=K, Na, or $NH_4$) as an oxidizing agent in 1.0 mL of water, followed by stirring at room temperature for 2 hours. The orange precipitate was collected, filtered under vacuum, and then washed with 100 mL of cold deionized water. The product was dried in hood overnight to obtain p-doped CPE (p-PFP, p-PFP-F or p-PFP-O) in 90-100% yield.

NMR chemical shift of each material was as follows.

The acronyms "WD," "MD," and "HD" after each material refer to the weakly, moderately, and highly doped states, respectively, as a relative doped state. In this specification, the omission of such acronym may be understood as "–MD" (moderately doped), unless otherwise specified.

p-PFP-WD. $^1$H NMR (600 MHz, DMSO-$d_6$, $\delta_{ppm}$): 8.10-7.38 (m, 10H), 2.20 (br, 8H), 1.39 (br, 4H), 0.66 (br, 4H); $^{13}$C NMR (150 MHz, DMSO-$d_6$, $\delta_{ppm}$): 151.5, 139.7, 139.4, 138.9, 129.1, 127.5, 127.0, 125.8, 121.2, 120.6, 55.0, 51.4, 25.5, 23.3.

p-PFP-MD (or p-PFP). $^1$H NMR (600 MHz, DMSO-$d_6$, $\delta_{ppm}$): 8.10-7.48 (m, 10H), 2.27 (br, 8H), 1.44 (br, 4H) 0.71 (br, 4H); $^{13}$C NMR (150 MHz, DMSO-$d_6$, $\delta_{ppm}$): 151.5, 139.4, 138.9, 129.1, 127.5, 127.2, 127.0, 125.8, 121.3, 120.7, 51.4, 25.4, 23.2.

p-PFP-HD. $^1$H NMR (600 MHz, DMSO-$d_6$, $\delta_{ppm}$): 8.20-7.40 (m, 10H), 2.21 (br, 8H), 1.40 (br, 4H), 0.56 (br, 4H); $^{13}$C NMR (150 MHz, DMSO-$d_6$, $\delta_{ppm}$): 174.6, 173.4, 168.7, 163.4, 130.2, 129.7, 129.5, 128.8, 127.2, 124.4, 72.2, 69.9, 51.2, 51.0, 50.5, 34.6, 32.8, 29.2, 20.8.

p-PFP-F. $^1$H NMR (600 MHz, DMSO-$d_6$, $\delta_{ppm}$): 7.99-7.64 (m, 9H), 2.27 (br, 4H), 2.09 (br, 4H), 1.42 (br, 4H) 0.68 (br, 4H); $^{13}$C NMR (150 MHz, DMSO-$d_6$, $\delta_{ppm}$): 162.3, 160.4, 158.8, 157.6, 151.6, 150.9, 148.2, 146.3, 141.4, 131.4, 127.0, 125.9, 123.6, 123.4, 121.5, 120.4, 114.4, 113.5, 51.2, 35.8, 25.5, 23.2.

p-PFP-O. 1H NMR (600 MHz, DMSO-$d_6$, $\delta_{ppm}$): 8.14-7.57 (m, 8H), 2.29 (br, 4H), 2.04 (br, 4H), 1.43 (br, 4H) 0.70 (br, 4H); $^{13}$C NMR (150 MHz, DMSO-$d_6$, $\delta_{ppm}$): 186.9, 162.4, 150.5, 150.1, 124.3, 120.2, 114.8, 79.2, 79.0, 56.5, 56.3, 55.5, 54.7, 54.4, 51.3, 35.8, 34.4, 30.8, 25.3, 24.9, 23.1.

Analysis Example 1

Characterization of CSEs

FIG. 12 shows electron spin resonance (ESR) spectra. In the non-oxidized DPF no signal appeared, while in the p-doped DPF treated with persulfate salt, $(NH_4)_2S_2O_8$ signal was observed. N-tertiary-butyl nitrone (PBN) was used as a spin trapping reagent. It is considered that a radical cation is generated in a main chain (backbone) of the p-DPF, resulting in an increase of the ESR signal intensity. Radical cation generated in the oxidized DPF main chain effectively generates a polaron-induced dipole. The sulfonate anion as a counter ion can stabilize the main chain that is positive charged (oxidized) and interacts via intramolecular or intermolecular coupling to form agglomerates.

Figure 2:
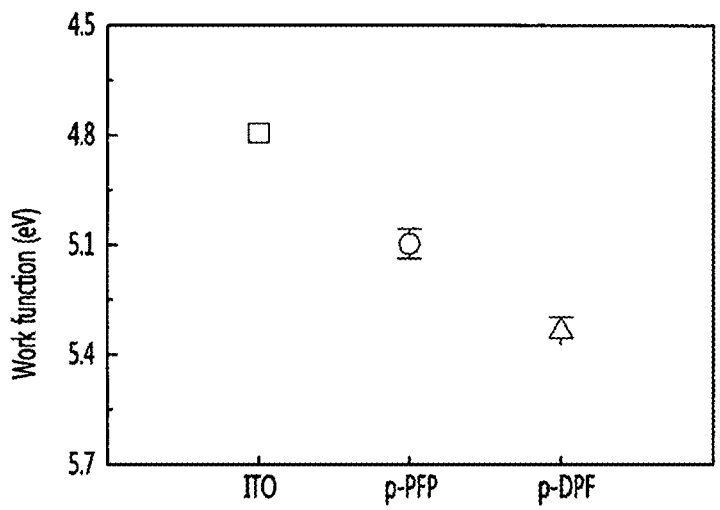
FIG. 2 shows a graph comparing work functions in the case of an ITO electrode, in the case of employing p-doped conjugated polyelectrolyte (p-PFP or p-CPE) as a hole transport layer, and in the case of employing p-doped conjugated small molecular electrolyte (p-DPF or p-CSE) as a hole transport layer, according to an embodiment of the present disclosure.
Figure 2:
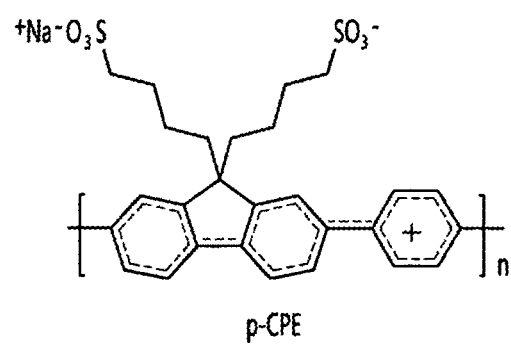
Figure 2:
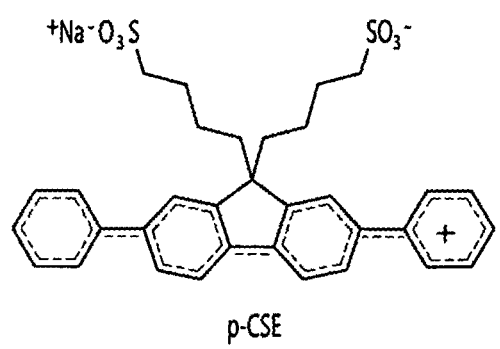

The work function was measured in the case of an ITO electrode without a hole transport layer, in the case of employing a hole transport layer comprising p-doped conjugated polyelectrolyte (p-CPE), i.e., p-PFP, and in the case of employing a hole transport layer comprising p-doped conjugated small molecular electrolyte (p-CSE), i.e., p-DPF, and the results are shown in Table 1 and FIG. 2.

TABLE 1

| Sample | WF (eV) | ΔWF (eV) |
|---|---|---|
| ITO(ref.) | 4.80 ± 0.03 | — |
| p-CPE | 5.10 ± 0.04 | 0.30 |
| p-CSE | 5.33 ± 0.03 | 0.53 |

In the case of p-CPE there is an increase in the work function by 0.30 eV compared with that of ITO, and in the case of p-CSE there is an increase in the work function by 0.53 eV compared with that of ITO. If several unit molecules consisting of polymer having same electric charge they generate repulsive forces. For this reason, it is most likely that only a portion of the unit molecules consisting of polymer is existed in a doped state, even if the oxidized polymer has positive charge. Whereas, in the case of small molecules, the repulsive force is less than that in polymer even if all the small molecules have positive charge. For this reason, it is most likely that all the small molecules exist in a doped state. Accordingly, it is considered that the p-doped small molecules generate more cations than those of p-doped polymer, which causes an effective dipole generation and an increase of the work function.

Figure 3:
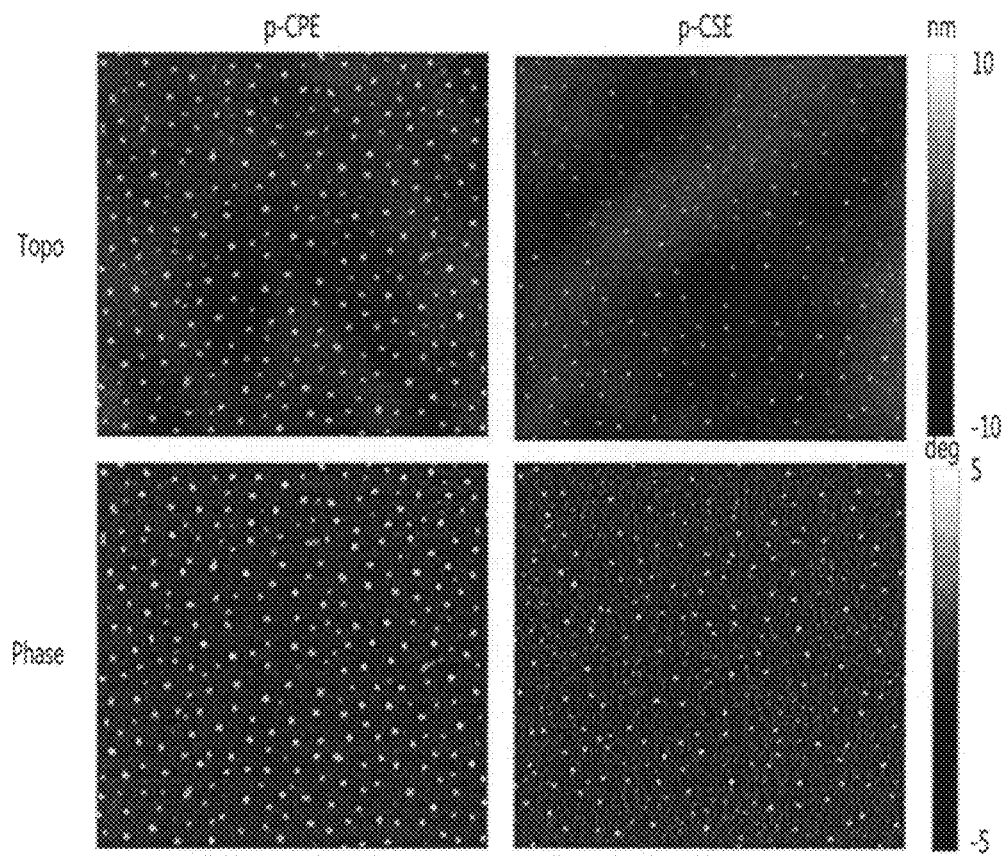
FIG. 3 shows AFM images of p-doped conjugated polyelectrolyte (p-PFP or p-CPE) and p-doped conjugated small molecular electrolyte (p-DPF or p-CSE) that are spin-coated on silicon substrate.
Figure 4:
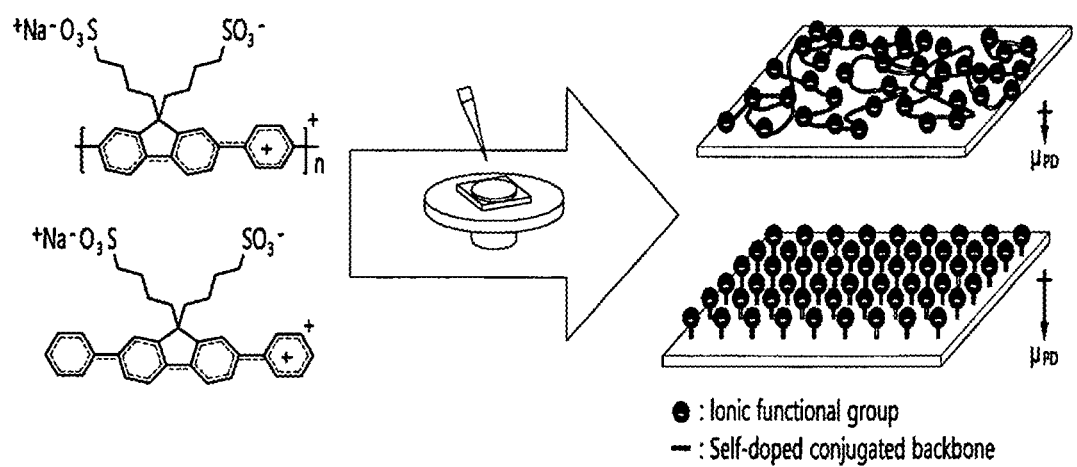
FIG. 4 is a schematic view illustrating the molecular alignment on the surface of the electrolyte in case that p-doped conjugated polyelectrolyte (p-PFP or p-CPE) or p-doped conjugated small molecular electrolyte (p-DPF or p-CSE) was spin-coated on silicon substrate.

Meanwhile, AFM images for p-doped conjugated polyelectrolyte (p-PFP or p-CPE) and p-doped conjugated small molecular electrolyte (p-DFP or p-CSE) as a hole transport material after spin-coated are shown in FIG. 3. Moreover, the molecular alignment on the surface of the electrolyte is schematically illustrated in FIG. 4. In a polyelectrolyte, the surfaces show agglomerates or are complicatedly tangled owing to the self-doping therebetween and the long chain structure. Whereas, in a small molecular electrolyte, the surface is not tangled compared with that of polymer but is well aligned. Such aligned molecular structure induces stronger dipole than polymer, which results more effective hole transportation between metal electrode and organic materials.

Preparation Example 1

Fabrication of Solar Cell

Example 1

To measure the change in the work function of metal electrode with p-doped CSEs, i.e., p-DFP, as a hole transport layer (HTL), a BHJ (Bulk Hetero Junction) solar cell was fabricated with the ITO/HTL/PTB7 (or PTB7-Th):$PC_{71}BM$/ETL/Al structure. Herein, the photoelectric conversion layer $PC_{71}BM$ means a polymer of [6,6]-phenyl $C_{71}$-butyric acid methyl ester, the photoelectric conversion layer comprises two donor polymer, PTB7 or PTB7-Th (see FIG. 10). A sol-gel based titanium oxide (TiOx) or PFN was used as an electron transport layer (ETL).

The p-DPF MeOH solution (0.02 wt %) was spin cast on ITO/glass substrate to form a 2 nm-thick film.

A solution, comprising a blend of PTB7 or PTB7-Th (1-Material, Inc.) as a donor and $PC_{71}BM$ (Solenne B.V.) as an acceptor (1:1.5 by weight) in a chlorobenzene/1,8-diiodooctane solvent mixture (97:3 by volume) with a total concentration of 25 mg/mL, was then spin cast on the p-DPF film to form a photoelectric conversion layer. A TiOx MeOH solution (TiOx:MeOH=1:300 by volume) or a PFN MeOH solution (with 0.1 wt % of PFN and small amount of acetic acid) was spin cast on the photoelectric conversion layer and then was baked at 80° C. in air for 10 mins. Finally, Al (100 nm) was deposited via thermal evaporation under high vacuum ($5 \times 10^{-7}$ Torr).

Figure 5:
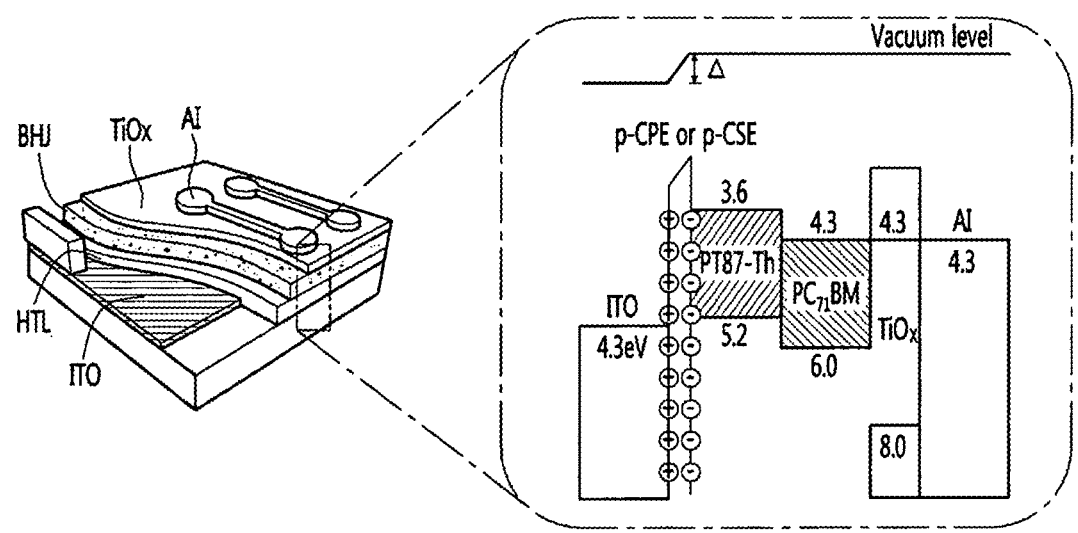
FIG. 5 illustrates a device structure and an energy diagram of a solar cell according to an embodiment of the present disclosure.

The structure of the device is shown in FIG. 5.

Comparative Example 1

For comparison, each of solar cells was prepared in the same manner as in Example 1 with exception that (1) the HTL was not prepared, (2) the HTL was prepared by spin casting an aqueous solution of PEDOT:PSS (Clevios AI 4083) instead of p-DPF on ITO/glass substrate, followed by baking at 150° C. in air for 10 mins to form a PEDOT:PSS film, or (3) the HTL was prepared by using p-CSE, i.e., p-PFP, instead of p-DPF, respectively.

Analysis Example 2

Characterization of Solar Cell

Figure 6:
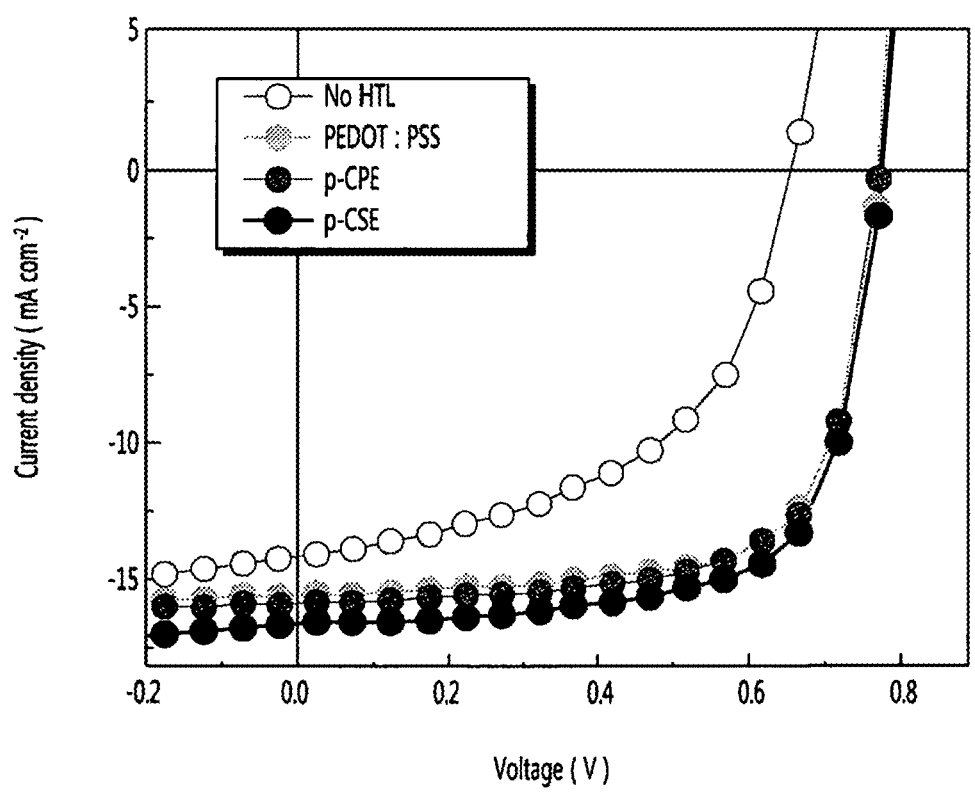
FIG. 6 shows a current density-voltage curve of solar cells employing respectively p-type conjugated small molecular electrolyte (p-CSE), p-type conjugated polyelectrolyte (p-CPE) and PEDOT:PSS, as a hole transport layers, according to an embodiment of the present disclosure.
Figure 7:
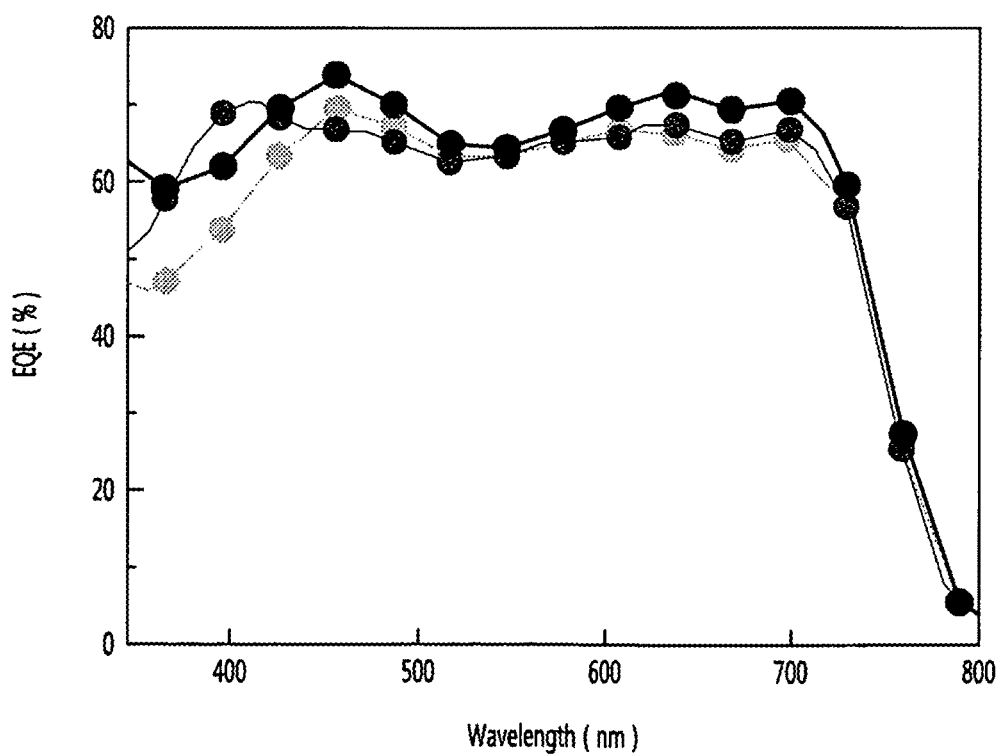
FIG. 7 shows EQE spectra of solar cells employing respectively p-type conjugated small molecular electrolyte (p-CSE), p-type conjugated polyelectrolyte (p-CPE) and PEDOT:PSS, as a hole transport layers, according to an embodiment of the present disclosure.

The effective work functions of various solar cells prepared in Preparation Example 1 and the parameters for the performance of the solar cells are summarized in Table 2, and the results of the evaluation are shown in FIG. 6 and FIG. 7.

TABLE 2

| HTL | WF (eV) | $V_{oc}$ (V) | $J_{sc}$ (mA/cm$^2$) | FF | PCE (%) |
|---|---|---|---|---|---|
| — | 4.8 | 0.67 | 14.1 | 53 | 4.7 |
| PEDOT:PSS | 5.1 | 0.78 | 15.5 | 72 | 8.7 |
| p-CPEs | 5.2 | 0.78 | 15.8 | 71 | 8.8 |
| p-CSEs | 5.3 | 0.78 | 16.5 | 70 | 9.0 |

As shown in Table 2, The solar cell using p-doped conjugated small molecular electrolyte as a hole transport layer exhibits a higher photoelectric conversion efficiency (PCE) than the solar cell using PEDOT:PSS or p-doped conjugated polyelectrolyte as a hole transport layer.

Preparation Example 2

Fabrication of Organic Light Emitting Diode (OLED)

Example 2

To evaluate a performance of an OLED with the p-doped CSEs as a hole transport layer (HTL), an OLED was fabricated with the ITO/p-DPF/Super Yellow/Ca/Al structure. Herein, poly(p-phenylene vinylene) derivative (Super Yellow, SY) was used as a light emitting layer.

The p-DPF methanol solution (0.5 wt %) was spin cast on ITO/glass substrate to form a film.

An aryl-substituted poly(p-phenylenevinylene) derivative (Super Yellow, Merck, Inc.) toluene solution (0.5 wt %) was spin cast on the p-DFP film to form a light emitting layer. Then the film was baked at 80° C. for 10 min in a glove box. Finally, an Al (100 nm)-capped Ca (20 nm) electrode was deposited via thermal evaporation under high vacuum ($5 \times 10^{-7}$ Torr).

Comparative Example 2

For comparison, an OLED was prepared in the same manner as in Example 2 with exception that an aqueous solution of PEDOT:PSS (Clevios AI 4083) or p-PFP instead of p-DPF was spin cast on ITO/glass substrate, dried at 150° C. (PEDOT:PSS) or 160° C. (p-PFP) in air for 10 mins, and then put into a glove box to form a light emitting layer.

Analysis Example 3

Characterization of OLED

Figure 8:
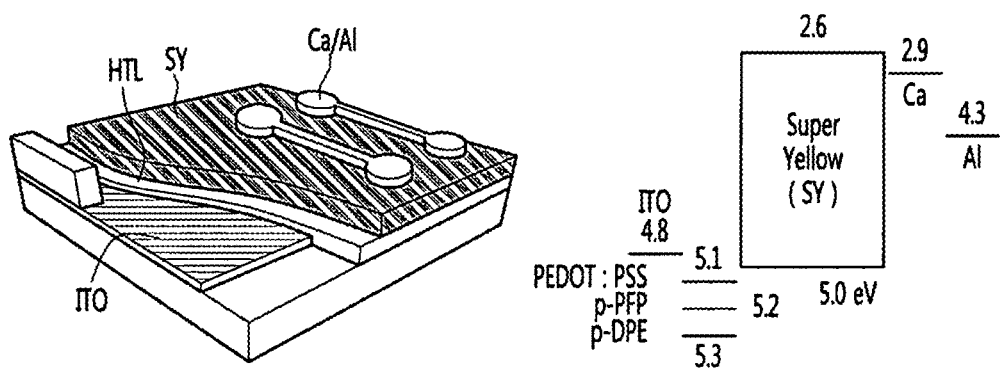
FIG. 8 illustrates a device structure and an energy diagram of an OLED according to an embodiment of the present disclosure.
Figure 11:
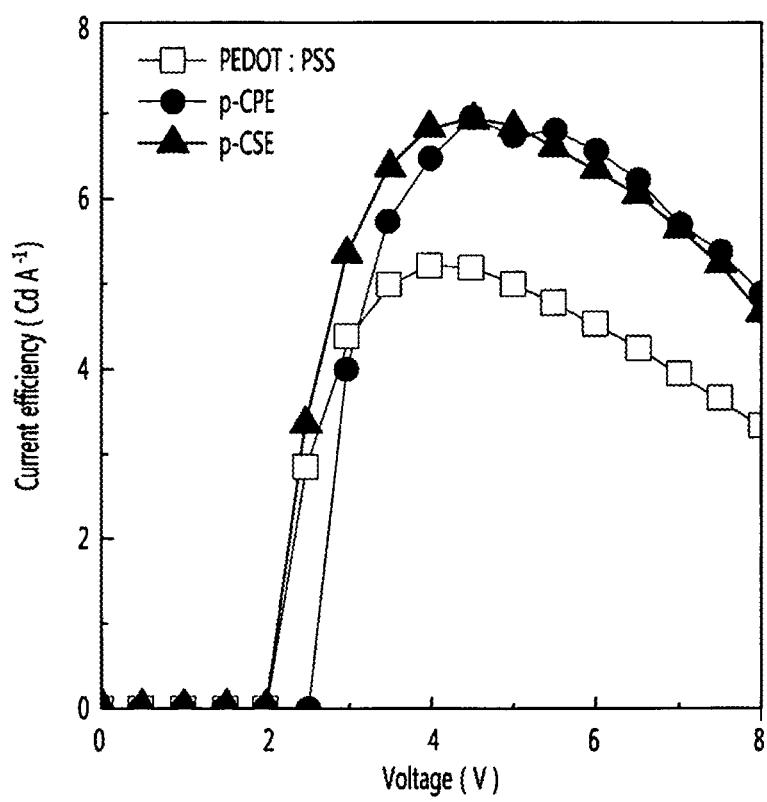
FIG. 11 shows a current efficiency-voltage curve of OLEDs employing respectively p-type conjugated small molecular electrolyte (p-CSE), p-type conjugated polyelectrolyte (p-CPE) and PEDOT:PSS, as a hole transport layers, according to an embodiment of the present disclosure.

The parameters for the performance of various OLEDs prepared in Preparation Example 2 are summarized in Table 3, and the results of the evaluation are shown in FIG. 8 and FIG. 11.

TABLE 3

| HTL | $V_{op}$ (V) | $L_{max}$ (Cd/m$^2$) | $CE_{max}$ (Cd/A) | $PE_{max}$ (lm/W) |
|---|---|---|---|---|
| PEDOT:PSS | 2.5 | 46,100 | 5.2 | 4.6 |
| p-CPEs | 2.5 | 40,650 | 6.9 | 5.1 |
| p-CSEs | 3.0 | 49,800 | 6.9 | 5.7 |

It can be seen that the p-doped CSEs used as a hole transport layer in OLED makes the flow of cations smooth.

Figure 9:
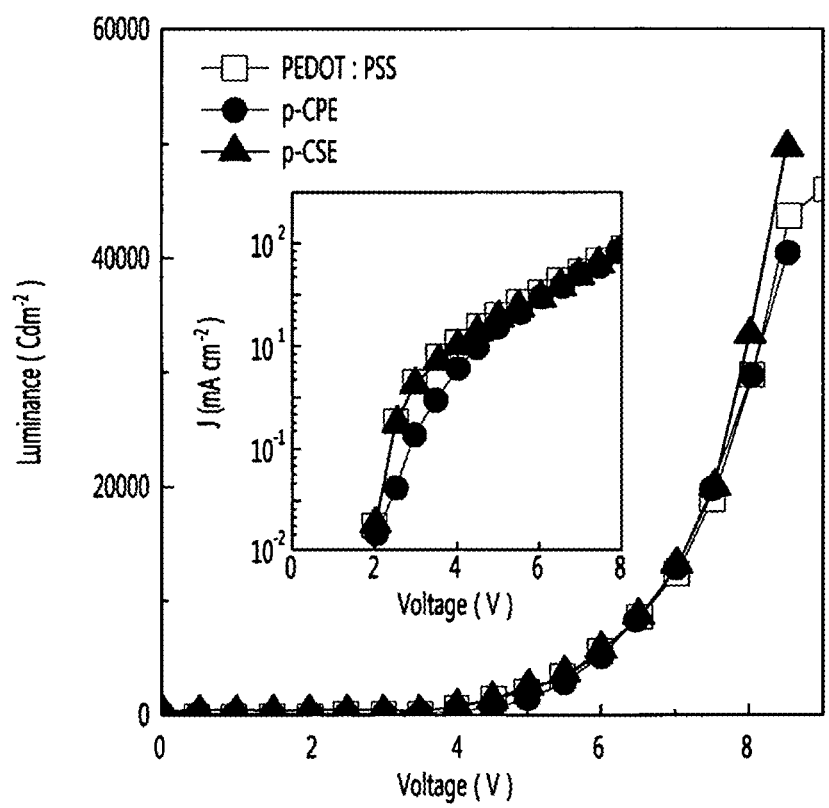
FIG. 9 shows a luminance-voltage curve of OLEDs employing respectively p-type conjugated small molecular electrolyte (p-CSE), p-type conjugated polyelectrolyte (p-CPE) and PEDOT:PSS, as a hole transport layers, according to an embodiment of the present disclosure.
Figure 10:
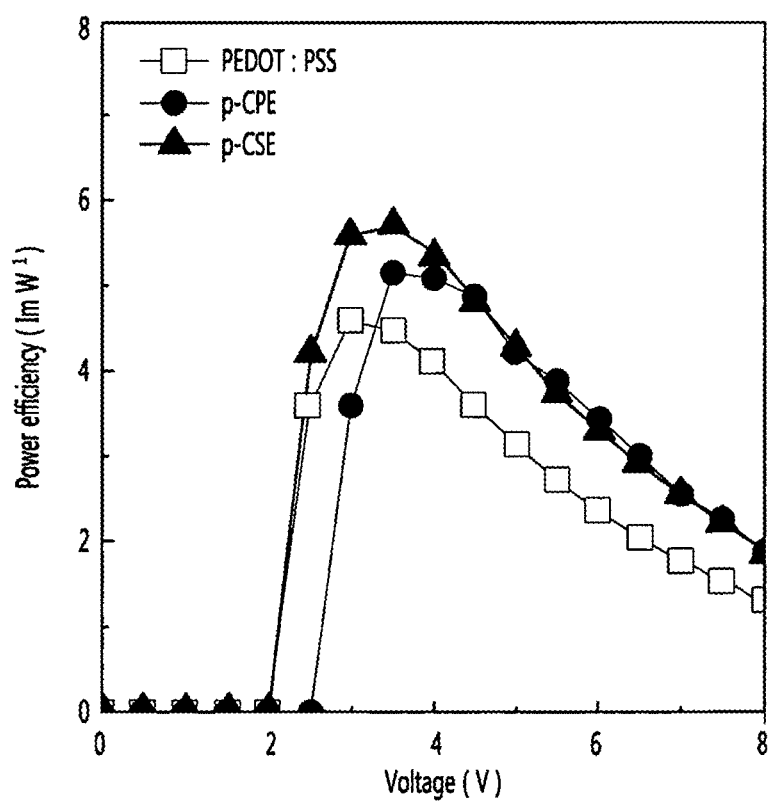
FIG. 10 shows a power efficiency-voltage curve of OLEDs employing respectively p-type conjugated small molecular electrolyte (p-CSE), p-type conjugated polyelectrolyte (p-CPE) and PEDOT:PSS, as a hole transport layers, according to an embodiment of the present disclosure.

Super Yellow based on the poly(p-phenylene) derivative was used as a light emitting layer as shown in FIG. 8. As shown in FIG. 9 to FIG. 11, the HTL using p-doped conjugated small molecular electrolyte was operated similar to or more effective than the HTL using most typical hole transport layer material (PEDOT:PSS or p-CPEs) and exhibited the highest luminous efficiency.

In conclusion, "hole-" and "electron-" transport layers are essential elements for various electronic devices based on metal/organic materials. PEDOT:PSS, which has been used mainly as a hole transport layer, has been pointed out the crucial problem of acidity of the material itself, and a conjugated polyelectrolyte has been yet commercialized practically owing to its batch-to-batch problem. However, the newly developed material, i.e., the conjugated small molecular electrolyte, is neutral and has advantages in more parts than any other material that has been used for a hole transport layer, thus it is considered as an innovative material. Further, since it consists of solution-processable organic materials, its industrial applicability expects to be very high, considering economical and technical possibilities.

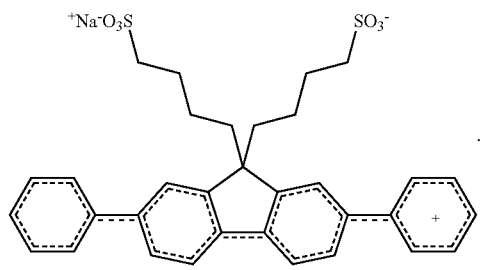

What is claimed is:

1. A p-doped conjugated small molecular electrolyte, wherein the p-doped conjugated small molecular electrolyte is a compound represented by Formula 5:

<Formula 5>